US012668772B2

(12) United States Patent
Bowman et al.

(10) Patent No.: US 12,668,772 B2
(45) Date of Patent: *Jun. 30, 2026

(54) MICROBIAL STEM CELL TECHNOLOGY

(71) Applicant: UNIVERSITY OF WYOMING, Laramie, WY (US)

(72) Inventors: Grant Bowman, Laramie, WY (US); Nikolai Mushnikov, Laramie, WY (US); Mark Gomelsky, Laramie, WY (US)

( * ) Notice: Subject to any disclaimer, the term of this patent is extended or adjusted under 35 U.S.C. 154(b) by 214 days.

This patent is subject to a terminal disclaimer.

(21) Appl. No.: 18/080,628

(22) Filed: Dec. 13, 2022

(65) Prior Publication Data

US 2023/0279339 A1     Sep. 7, 2023

Related U.S. Application Data

(62) Division of application No. 16/393,671, filed on Apr. 24, 2019, now Pat. No. 11,525,117.

(60) Provisional application No. 62/712,857, filed on Jul. 31, 2018, provisional application No. 62/661,818, filed on Apr. 24, 2018.

(51) Int. Cl.
| | |
|---|---|
| *C12N 1/20* | (2026.01) |
| *C07K 14/00* | (2006.01) |
| *C12N 15/86* | (2006.01) |
| *C12Q 1/6809* | (2018.01) |
| *C12Q 1/6865* | (2018.01) |
| *C12R 1/00* | (2006.01) |

(52) U.S. Cl.
CPC .............. *C12N 1/20* (2013.01); *C12N 15/86* (2013.01); *C12N 2529/10* (2013.01)

(58) Field of Classification Search
CPC .................................. C12N 1/20; C12N 15/86
See application file for complete search history.

(56) References Cited

PUBLICATIONS

Santos et al., Molecular Microbiology, 92(5), 985-1004, 2014.*
Office Action for U.S. Appl. No. 16/393,671 dated Apr. 15, 2022.
Bowman GR, Comolli LR, Gaietta GM, et al. Caulobacter PopZ forms a polar subdomain dictating sequential changes in pole composition and function. Mol Microbiol. 2010;76(1):173-189. doi:10.1111/j.1365-2958.2010.07088.
Bowman GR, Comolli LR, Zhu J, et al. A polymeric protein anchors the chromosomal origin/ParB complex at a bacterial cell pole. Cell. 2008;134(6):945-955.
Romling U, Galperin MY, Gomelsky M. Cyclic di-GMP: the first 25 years of a universal bacterial second messenger. Microbiol Mol Biol Rev. 2013;77(1):1-52. doi:10.1128/MMBR.00043-12.
Kalscheuer, R. et al. Neutral Lipid Biosynthesis in Engineered *Escherichia coli* : Jojoba Oil-Like Wax Esters and Fatty Acid Butyl Esters. Appl. Environ. Microbiol. 72, 1373-1379 (2006).

Olson, E. J., Hartsough, L. A., Landry, B. P., Shroff, R. & Tabor, J. J. Characterizing bacterial gene circuit dynamics with optically programmed gene expression signals. Nat. Methods 11, 449-455 (2014).
Tsoi, R. et al. Metabolic division of labor in microbial systems. Proc. Natl. Acad. Sci. U. S. A. 201716888 (2018). doi:10.1073/pnas.1716888115.
Campbell K, Xia J, Nielsen J. 2017. The Impact of Systems Biology on Bioprocessing. Trends Biotechnol 35:1156-1168.
Heyland J, Blank LM, Schmid A. 2011. Quantification of metabolic limitations during recombinant protein production in *Escherichia coli*. J Biotechnol 155:178-184.
Rugbjerg P, Myling-Petersen N, Porse A, Sarup-Lytzen K, Sommer MOA. 2018. Diverse genetic error modes constrain large-scale bio-based production. Nat Commun 9:787.
Mierendorf RC, Morris BB, Hammer B, Novy RE. 1998. Expression and Purification of Recombinant Proteins Using the pET System. Methods Mol Med 13:257-292.
Gomelsky M, Galperin MY. 2013. Bacterial second messengers, cGMP and c-di-GMP, in a quest for regulatory dominance. EMBO J 32:2421-2423.
Chen L-H, Koseo?lu VK, Güvener ZT, Myers-Morales T, Reed JM, D'Orazio SEF, Miller KW, Gomelsky M. 2014. Cyclic di-GMP-dependent signaling pathways in the pathogenic Firmicute Listeria monocytogenes. PLoS Pathog 10:e1004301.
Ryu M-H, Gomelsky M. 2014. Near-infrared light responsive synthetic c-di-GMP module for optogenetic applications. ACS Synth Biol 3:802-810.
Zeng A-P. 2019. New bioproduction systems for chemicals and fuels: Needs and new development. Biotechnol Adv.
Nikel PI, de Lorenzo V. 2018. Pseudomonas putida as a functional chassis for industrial biocatalysis: From native biochemistry to trans-metabolism. Metab Eng 50:142-155.
Wawrousek K, Noble S, Korlach J, Chen J, Eckert C, Yu J, Maness P-C. 2014. Genome annotation provides insight into carbon monoxide and hydrogen metabolism in Rubrivivax gelatinosus. PloS One 9:e114551.
Kalscheuer R, Stolting T, Steinbuchel A. 2006. Microdiesel: *Escherichia coli* engineered for fuel production. Microbiol Read Engl 152:2529-2536.

(Continued)

*Primary Examiner* — Maryam Monshipouri
(74) *Attorney, Agent, or Firm* — Patterson + Sheridan, LLP

(57)     ABSTRACT

The present disclosure relates to microbial stem cell technology that enables a growing microbial culture to stably maintain two or more distinct cell types in a ratio that can be genetically programmed and/or dynamically controlled during cultivation. It is contemplated that embodiments described herein can be utilized to increase product yield in microbial fermentations and advanced engineering of biomaterials using genetically engineered microbial cells, among others.

6 Claims, 18 Drawing Sheets
(18 of 18 Drawing Sheet(s) Filed in Color)
Specification includes a Sequence Listing.

(56) References Cited

PUBLICATIONS

Sherkhanov S, Korman TP, Clarke SG, Bowie JU. 2016. Production of FAME biodiesel in *E. coli* by direct methylation with an insect enzyme. Sci Rep 6:24239.

Nawabi P, Bauer S, Kyrpides N, Lykidis A. 2011. Engineering *Escherichia coli* for biodiesel production utilizing a bacterial fatty acid methyltransferase. Appl Environ Microbiol 77:8052-8061.

Ennen RM, Kruziki MA, Kumar K, Zinkel RA, Burnum KE, Lipton MS, Hoover SW, Ranatunga DR, Wittkopp TM, Marner WD, Pfleger BF. 2011. Membrane stresses induced by overproduction of free fatty acids in *Escherichia coli*. Appl Environ Microbiol 77:8114-8128.

Zhang Y-M, Rock CO. 2008. Membrane lipid homeostasis in bacteria. Nat Rev Microbiol 6:222-233.

Jee J, Rasouly A, Shamovsky I, Akivis Y, Steinman SR, Mishra B, Nudler E. 2016. Rates and mechanisms of bacterial mutagenesis from maximum-depth sequencing. Nature 534:693-696.

Iost I, Guillerez J, Dreyfus M. 1992. Bacteriophage T7 RNA polymerase travels far ahead of ribosomes in vivo. J Bacteriol 174:619-622.

Mairhofer J, Scharl T, Marisch K, Cserjan-Puschmann M, Striedner G. 2013. Comparative transcription profiling and in-depth characterization of plasmid-based and plasmid-free *Escherichia coli* expression systems under production conditions. Appl Environ Microbiol 79:3802-3812.

Luo X, Yang Y, Ling W, Zhuang H, Li Q, Shang G. 2016. Pseudomonas putida KT2440 markerless gene deletion using a combination of ? Red recombineering and Cre/loxP site-specific recombination. FEMS Microbiol Lett 363.

Szafranski P, Mello CM, Sano T, Smith CL, Kaplan DL, Cantor CR. 1997. A new approach for containment of microorganisms: dual control of streptavidin expression by antisense RNA and the T7 transcription system. Proc Natl Acad Sci U S A 94:1059-1063.

Bagdasarian M, Lurz R, Ruckert B, Franklin FC, Bagdasarian MM, Frey J, Timmis KN. 1981. Specific purpose plasmid cloning vectors. II. Broad host range, high copy number, RSF1010-derived vectors, and a host-vector system for gene cloning in Pseudomonas. Gene 16:237-247.

Samanta A, Podder S, Ghosh CK, Bhattacharya M, Ghosh J, Mallik AK, Dey A, Mukhopadhyay AK. 2017. ROS mediated high antibacterial efficacy of strain tolerant layered phase pure nano-calcium hydroxide. J Mech Behav Biomed Mater 72:110-128.

Sur DH, Mukhopadhyay M. 2018. Role of zinc oxide nanoparticles for effluent treatment using Pseudomonas putida and Pseudomonas aureofaciens. Bioprocess Biosyst Eng.

Inaba, M. & Yamashita, Y. M. Asymmetric stem cell division: Precision for robustness. Cell Stem Cell 11, 461-469 (2012).

Kysela, D.T. et al. Biological consequences and advantages of asymmetric bacterial growth. Annu Rev Microbiol 417-435 (2013).

Tsokos, C. G. & Laub, M. T. Polarity and cell fate asymmetry in Caulobacter crescentus. Curr. Opin. Microbiol. 15, 744-750 (2012).

Grünenfelder, B. et al. Proteomic analysis of the bacterial cell cycle. Proc. Natl. Acad. Sci. U. S. A. 98, 4681-4686 (2001).

Werner, J. N. et al. Quantitative genome-scale analysis of protein localization in an asymmetric bacterium. Proc. Natl. Acad. Sci. 106, 7858-7863 (2009).

Eichenberger, P. et al. The program of gene transcription for a single differentiating cell type during sporulation in Bacillus subtilis. PLoS Biol. 2, (2004).

Jones JA, Wang X. Use of bacterial co-cultures for the efficient production of chemicals. Curr. Opin. Biotechnol. 33-38 (2017).

Bowman, G. R. et al. Oligomerization and higher-order assembly contribute to sub-cellular localization of a bacterial scaffold. Mol. Microbiol. 90, 776-95 (2013).

Ebersbach, G., Briegel, A., Jensen, G. J. & Jacobs-Wagner, C. A self-associating protein critical for chromosome attachment, division, and polar organization in Caulobacter. Cell 134, 956-968 (2008).

Coquel, A. S. et al. Localization of protein aggregation in *Escherichia coli* is governed by diffusion and nucleoid macromolecular crowding effect. PLoS Comput. Biol. 9, e1003038 (2013).

Lloyd-Price, J. et al. Asymmetric disposal of individual protein aggregates in *Escherichia coli*, one aggregate at a time. J. Bacteriol. 194, 1747-1752 (2012).

Scheu, K., Gill, R., Saberi, S., Meyer, P. & Emberly, E. Localization of aggregating proteins in bacteria depends on the rate of addition. Front. Microbiol. 5, 1-5 (2014).

Jenal, U., Reinders, A. & Lori, C. Cyclic di-GMP: Second messenger extraordinaire. Nat. Rev. Microbiol. 15, 271-284 (2017).

Chou, S. H. & Galperin, M. Y. Diversity of cyclic di-GMP-binding proteins and mechanisms. J. Bacteriol. 198, 32-46 (2016).

Ryjenkov, D. A., Simm, R., Romling, U. & Gomelsky, M. The PilZ domain is a receptor for the second messenger c-di-GMP. The PilZ domain protein YcgR controls motility in enterobacteria. J. Biol. Chem. 281, 30310-30314 (2006).

Holmes, J. A. et al. Caulobacter PopZ forms an intrinsically disordered hub in organizing bacterial cell poles. Proc. Natl. Acad. Sci. 113, 12490-12495 (2016).

Boehm, A. et al. Second Messenger-Mediated Adjustment of Bacterial Swimming Velocity. Cell 141, 107-116 (2010).

Chin, K. H. et al. Structural polymorphism of c-di-GMP bound to an EAL domain and in complex with a type II PilZ-domain protein. Acta Crystallogr. Sect. D Biol. Crystallogr. 68, 1380-1392 (2012).

Cabantous, S. et al. A new protein-protein interaction sensor based on tripartite split-GFP association. Sci. Rep. 3, 2854 (2013).

Shekhawat, S. S. & Ghosh, I. Split-protein systems: Beyond binary protein-protein interactions. Curr. Opin. Chem. Biol. 15, 790-797 (2011).

Ryjenkov, D. A., Tarutina, M., Moskvin, O. V. & Gomelsky, M. Cyclic diguanylate is a ubiquitous signaling molecule in bacteria: Insights into the biochemistry of the GGDEF protein domain. J. Bacteriol. 187, 1792-1798 (2005).

* cited by examiner

MG-1655 ΔyhjH                    MG-1655                    MG-1655 ΔyhjH araBADp-yhjH-
                                                             mChy-popZ BphS (DGC)

Slr (DGC)

Number of YhjH-mChy-PopZ foci per cell

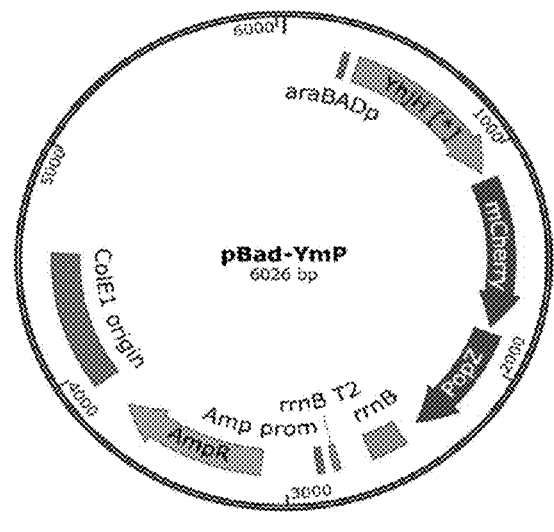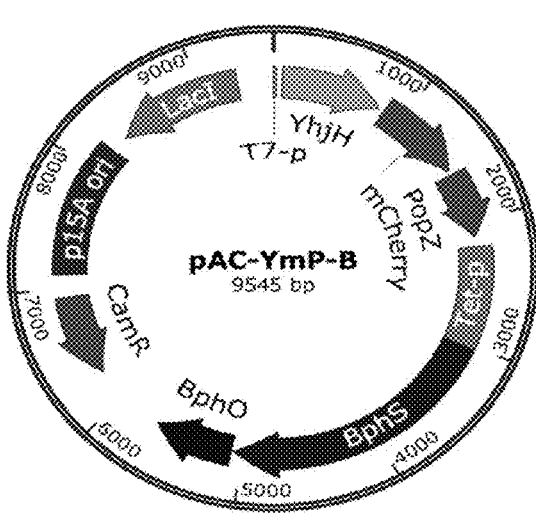
FIG. 5A
FIG. 5B
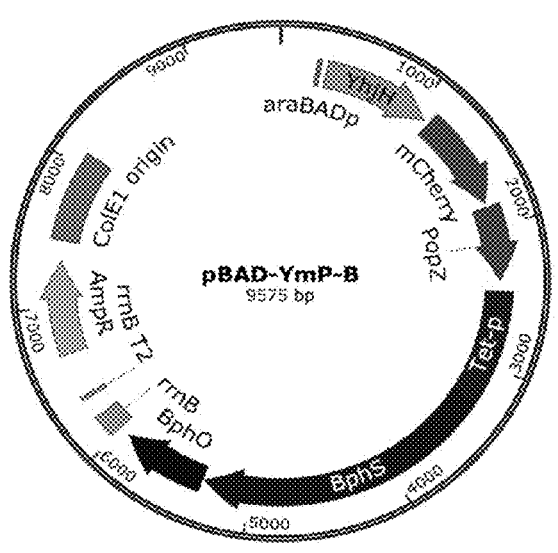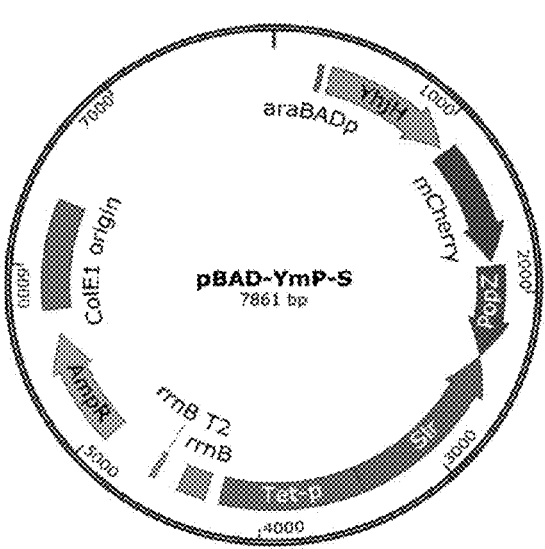
FIG. 5C
FIG. 5D

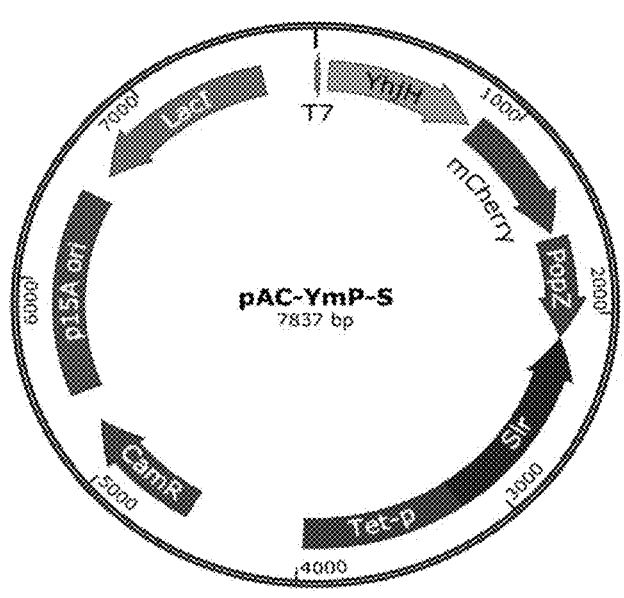
FIG. 5E
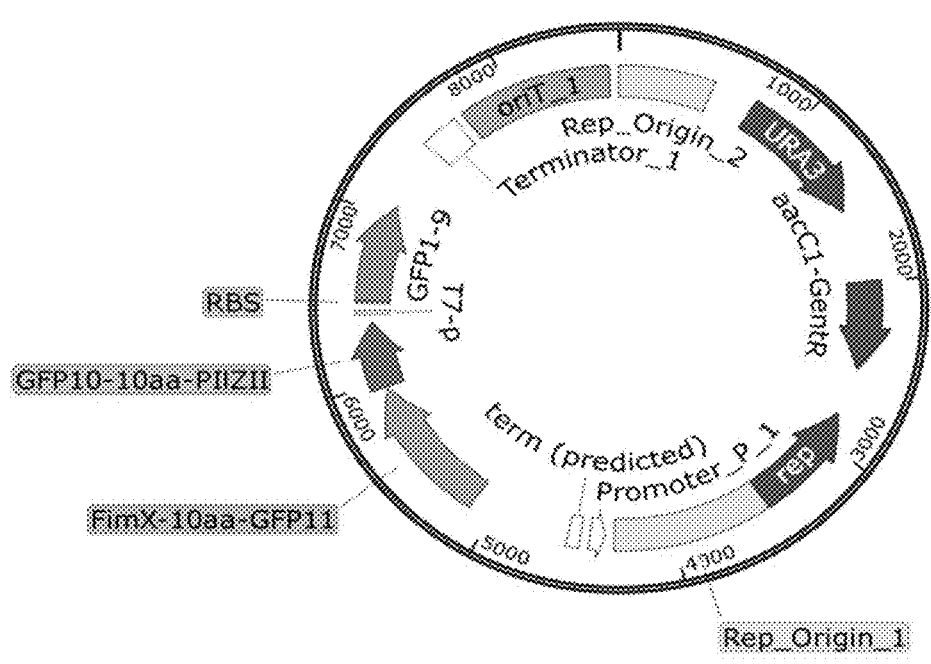
FIG. 5F     pMQ132_split GFP rep
8599 bp pB-Mrk-rbsGFP
6168 bp

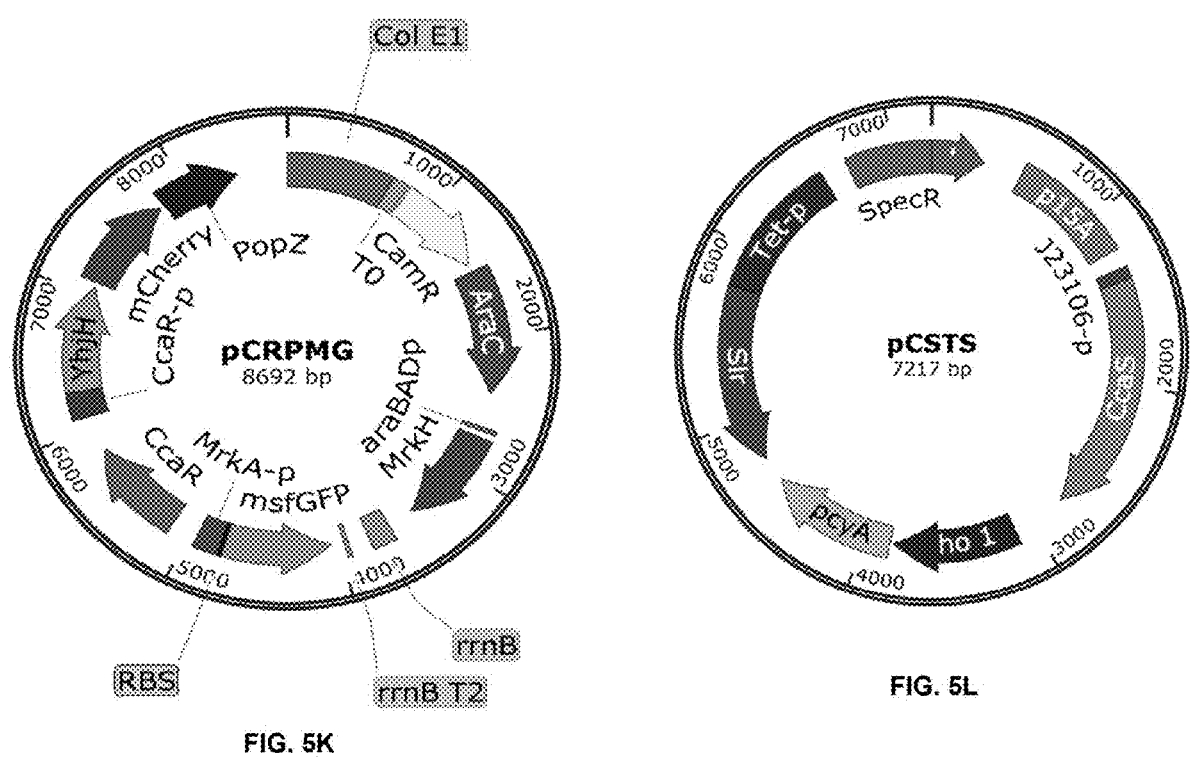
FIG. 5K
FIG. 5L
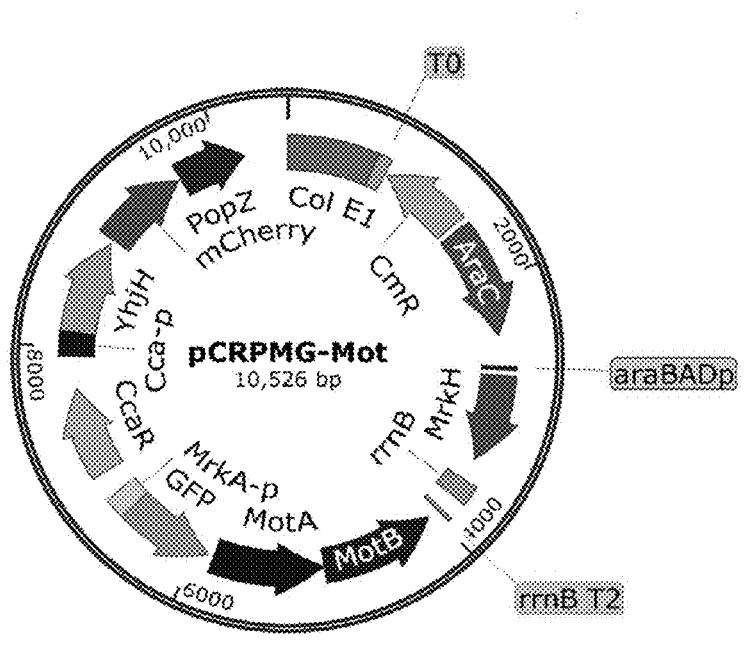
FIG. 5M

FIG. 5N                                          FIG. 5O

SEQUENCE LISTING

```
Sequence total quantity: 32
SEQ ID NO: 1              moltype = DNA  length = 1481
FEATURE                  Location/Qualifiers
source                   1..1481
                         mol_type = other DNA
                         organism = Synthetic construct
SEQUENCE: 1
tagttcagga cgtgctcaac taccccagga aagtgagttt ttaagaaata gtcttcccag  60
ttgatagcgc gaggatcaaa atagaacatg tcagcctcta cgatcgattc cttggcagca  120
atacgtaact tctcagtatt catgtcgtca aagatacctt ggaagaacaa gtaaggcttg  180
tagatgtcaa ccagacgtaa cagcaagcgc gttttacgct tcaagtccat gtacttccct  240
ttgaaccact gacaaaagat ggtgtttgca atctctaaca ccttcagagg cagtaagaaa  300
ttcaaagtca agtataagtg aaaggtacta aagcttgaga acaccatagc gcgaccaaca  360
tgcacggggt tacgatcggg attgatccaa ggattcttcg tgaaatagcg gtgtgccatt  420
tccggcagcg cggacagttt catggggtta gcagcgctgg accccacgtg gtacgtaact  480
ggttccacat aacgctggtt agcatgcgct accatcgcaa caatcgtcgc attcacaacc  540
atatccgccg gaatcagatc gataatagtc gacggaccac acaacatgca gcgaaggcga  600
cctttccat agtataccgg aacattatcg atggtgcgta cgccttcaac ccatcctgga  660
aagggttcct taaacgtact ggtgataata gtggggcgaa taattgtcaa agggatgtct  720
```

-continued

```
cccttgtact gcatcaacaa catctcaccc agcgcttttg tgaagacata aacattaggc   780
caccccaat  gacgagcacg ctcgatcccc atatccttca tagtgctttt aatggacttc   840
tccgtagccc ctgcggcttg aagttcattg attttagctt cgactaactt tttctccacg   900
ttaatatcca aaccaaggcg gccattcaat gactccccca tgtagtacgg cttttctaaa   960
atcagcccgt tcttttcgcc ggatacatat gctgtgctta catgaacaaa aatcttcagc  1020
ttgttacatt ttttggcaaa atctaagacg tatttagccc catatgtatt aataagcagg  1080
gatacatcgt aacgctcaat aaaattgatg gtagcggcta agttcaccac aacgtcaatt  1140
tcgcgccaca tttcttcctt taagttcaca tctttaaggc acaagtcttc gcccgtgatg  1200
tctcccggca cgactgttac tttttcgctt acgaaactgt aaaaattggc acccaagttt  1260
tgcttaagta ccttgaacaa ttccttgcca aacacttcgt tctgtaaacg cagggcagcc  1320
gtttcatcgt ctgtcgcacg caataataag tacaatttct taacattcgg ttgcgaacgc  1380
aacactttt  ccacgaagat cttggcaagg gagccggtag cccctgtgac aaggatcgcc  1440
ttgttatcca gaaactcaag gatggaaccc atctcttcca t                     1481
```

SEQ ID NO: 2                moltype = DNA   length = 28
FEATURE                     Location/Qualifiers
source                      1..28
                            mol_type = other DNA
                            organism = Synthetic construct
SEQUENCE: 2
```
gacgcttttt atcgcaactc tctactgt                                       28
```

SEQ ID NO: 3                moltype = DNA   length = 600
FEATURE                     Location/Qualifiers
source                      1..600
                            mol_type = other DNA
                            organism = Rhodobacter sphaeroides
SEQUENCE: 3
```
atggctagac ccctttcccg cgatcttcgc gagaagacgg gcatgctcca caaccgggcc   60
gaaacgctcc tcggcttgcc aagcggcatc atgggcgcgg ccgattacgt ggattggctt  120
cggcattttc tagccttgta cgatccgatc gaacgtagga ttgtggcctt tggaggctgg  180
agcgggttgg catccttcga ccctgacccg ggccattcgc ggcgcctgat ccaggatctg  240
cacgcccttg gcatcgacac cgaccgcatc ccgcgagcac cggccgaata ctgcccgccg  300
ctcacgaact tcgcccgggc gctcggccgcc cgctatgtgc tcgagggctc tgcgcttggc  360
ggcagggtca tcctgcatca tctgaagaag cgcatcggac acgaaatcgg gaatgcgact  420
gccttctttg gcggcccgtc ccacgggacc gcgacgcact ggcgtgcctt ccaggctgcg  480
ctggaccggt tcggtgcggc acatcccgac aagagggcgg atgtgctggc cggcgccgcc  540
gcgaccttca cggcgctcct cgaatggttc accccttttg tggcagcccg gcgggtatga  600
```

SEQ ID NO: 4                moltype = DNA   length = 2052
FEATURE                     Location/Qualifiers
source                      1..2052
                            mol_type = other DNA
                            organism = Rhodobacter sphaeroides
SEQUENCE: 4
```
atggctagag ggtgcctcat gacgatctct gggggcacct cgacccttc gatctgcgag    60
atggaaccga tcgccacgcc cggcgcgatc cagccgcacg gagcgctgat gaccgcgcgg  120
gccgacagcg gccgcgtcgc ccatgccagc gtcaacttgg gcgagatcct cggcctgccc  180
gcggcctcgg ttctgggggc gcccatcgga gaggtgatcg ggcgcgtcaa cgagatcttg  240
ctgcgcgagg cgcgtcgtag cggctccgag acgccggaaa caatcgggtc cttccgcaga  300
agcgacggac agctgctgca tctccatgcg ttccagtcgg gcgactacat gtgcctcgac  360
atcgagccgg tgcgcgatga ggatggccgg ctccctccgg gagccaggca atcggttatc  420
gagaccttct ccagcgccat gacgcaggtg gaactctgcg agctcgcggt tcacgggctg  480
cagctggtgc tgggctatga ccgggtgatg gcctatcgct tcggcgctga cggacatggc  540
gaggttatcg ccgagcggcg ccggcaggat ctcgagcctt acctggggct gcactacccg  600
gcatcggaca ttccgcaaat cgcgcgcgcg ctctacctgc gccagagggt gggtgccatt  660
gcggatgcgt gctaccggcc ggttccgttg ctcggccatc ccgagctcga cgacggcaag  720
cccctcgacc tgacgcacag ttcgctgcgc agcgtctcgc cggtccatct cgactacatg  780
cagaacatga acacggcggc cagcctgacc atcgggctgg ccgacggcga caggctgtgg  840
gggatgctgg tctgccacaa cacgacccc  cgtattgccg gccccgagtg gcgtgcggcg  900
gcgggcatga tcgggcaagt ggtctcgctg ctcctgagcc ggctgggcga ggtcgagaat  960
gccgccgaga cactggcccg gcagtcgacg ctctcgacgc tggtcgaacg gctatcgacc 1020
ggtgatacgc tggctgcggc atttgtcgcg gcagatcagc tgatcctcga tctggtcgga 1080
gccagtgccg cggtcgtgcg gctggtcgga caggaattgc acttcgggcg gacgcgcggg 1140
gtcgatgcga tgcagaaggt cctggacagt ctgggtcgcc cctcgcccct ggaggtgctg 1200
tccctcgacg acgtcaccct gcgccatccc gagctgccag agctgctggc ggccggaagc 1260
ggcatcctgc tgctcccccct gacatccggg gacgagatc  tgatcgcctg gttccgccct 1320
gagcatgtgc agacgatcac ctgggggtggc aatccggccg aacatggcac ttggaacccg 1380
gcaacgcagc ggatgagacc gcgcgcctcg ttcgacgcct ggaaggagac agtcaccggc 1440
cgctcgcttc cctggacctc cgccgagcga aattgcgcgc gcgagctggg tgaggcgatc 1500
gccgccgaga tggcgcagcg aactcgggcc gaagaacttg aaagggtggc catggtcgat 1560
agcttaacaa gactctggaa ccgtttgggc attgaaactc ttctaaaacg ggaatgggag 1620
tacgctaccc gcaaaaattc tcctatttcc attgtcatga ttgattttga caactttaaa 1680
caaatcaacg atcaacacgg tcatttagtc ggagcaggg  ttctgcaggg tagtgcccgt 1740
ttaatcattt cagttcttgc ttcctacgat attttgggca gatgggagg  agatgagttc 1800
atgcttattc tgcctggttc tggtcgggag cagaccgctg tgctcctaga aagaattcaa 1860
gccaccattg cccaaaaccc agtacccaca tctgcgggac ccatggcaat cagcttgagt 1920
atggggggag tcagtgtatt taccaaccag ggtgaagcac tccagtattg ggtagaacag 1980
gcagataatc agttgatgaa agtcaaacgt cttggtaagg gcaattttca actggcagaa 2040
```

-continued

```
taccaattgt ga                                                    2052

SEQ ID NO: 5             moltype = DNA   length = 660
FEATURE                  Location/Qualifiers
source                   1..660
                         mol_type = unassigned DNA
                         organism = unidentified
SEQUENCE: 5
ttacgccccg ccctgccact catcgcagta ctgttgtaat tcattaagca ttctgccgac  60
atggaagcca tcacagacgg catgatgaac ctgaatcgcc agcggcatca gcaccttgtc  120
gccttgcgta taatatttgc ccatagtgaa aacgggggcg aagaagttgt ccatattggc  180
cacgtttaaa tcaaaactgg tgaaactcac ccagggattg gctgagacga aaaacatatt  240
ctcaataaac cctttaggga aataggccag gtttttcaccg taacacgcca catcttgcga  300
atatatgtgt agaaactgcc ggaaatcgtc gtggtattca ctccagacg atgaaaacgt  360
ttcagtttgc tcatggaaaa cggtgtaaca agggtgaaca ctatcccata tcaccagctc  420
accgtctttc attgccatac ggaactccgg atgagcattc atcaggcggg caagaatgtg  480
aataaaggcc ggataaaaact tgtgcttatt tttctttacg gtctttaaaa aggccgtaat  540
atccagctga acggtctggt tataggtaca ttgagcaact gactgaaatg cctcaaaatg  600
ttctttacga tgccattggg atatatcaac ggtggtatat ccagtgattt ttttctccat  660

SEQ ID NO: 6             moltype = DNA   length = 705
FEATURE                  Location/Qualifiers
source                   1..705
                         mol_type = other DNA
                         organism = Synechocystis sp.
SEQUENCE: 6
atgagaattc ttttagtgga ggatgatttg ccgctggcgg aaaccccttgc tgaagcattg  60
agtgaccagc tttacaccgt tgatattgcc accgacgctt ccctcgcctg ggactatgcc  120
tcccgactgg aatatgacct cgttattttg gatgtgatgc tgccggagtt ggacgggatt  180
accctctgtc aaaaatggcg atcgcacagt tatttaatgc caattttgat gatgacagcc  240
agggatacga tcaatgataa aatcacgggc ttggatgcgg gggcggatga ttatgtggtc  300
aagccagtgg atttgggggga gttatttgcc agggtgcgag ctttgttgcg tcgggggttgt  360
gcaacgtgcc aaccagtttt agagtgggggg ccaatcaggt tggatccaag cacctatgaa  420
gttagttatg acaatgaggt tttgtctttg acccgcaagg aatacagcat tctggaatta  480
ctactccgca atggccgtcg ggtgctaagt cggagcatga ttatcgatag tatctggaag  540
ttggagagtc ccccagagga agatacggtt aaggtgcatg tgcggagttt gcgacaaaaa  600
ttaaaaagtg ccggtttatc agcagatgcc attgaaacgg tccatggcat tgggtatcgt  660
ctggccaatt taacggaaaa atctttgtgc caagggaaaa actag                  705

SEQ ID NO: 7             moltype = DNA   length = 190
FEATURE                  Location/Qualifiers
source                   1..190
                         mol_type = other DNA
                         organism = Synechocystis sp.
SEQUENCE: 7
agcccattgt gctttctct atcaacctca gcttacctga aggggtgaac aggtctgggt  60
taattcatgt tgcgaaatgt aacagtttta gtcgcatcag ctaactttcc gatttcttta  120
cgatttctc ccccttttct tcaattttac tttgttagga tcgcatttttt aaaagagga  180
gaaatactag                                                       190

SEQ ID NO: 8             moltype = DNA   length = 1389
FEATURE                  Location/Qualifiers
source                   1..1389
                         mol_type = other DNA
                         organism = Synechocystis sp.
SEQUENCE: 8
atggcaaat ttctaattcc aatcgaattt gtttttctgg cgatcgccat gacctgttat  60
ttatggcaca gacaaaacca agaacgccgc aggattgaaa ttagcatcaa gcaacaaacc  120
caacgggaac gatttattaa ccaaattacc caacatatcc gccaatcgtt aaacttggaa  180
acggttttaa ataccaccgt cgctgaagtt aaaaccctgt tgcaagttga tcgagttcta  240
atttatcgca tttggcaaga tggcacgggc agcgccatta cggaatcggt gaatgccaat  300
tatcctagta ttttagggcg gacctttttcc gatgaagttt ttcccgttga ataccatcaa  360
gcctacacca aaggtaaagt acgggccatt aatgacattg accaggatga catagagatt  420
tgcctagctg atttcgtcaa acaatttggc gtgaaatcaa aattagtagt gcccattctt  480
caacataatc gtgcttcttc cctagataat gaatcagaat ttccctatct ttggggggctg  540
ttaattaccc atcaatgtgc tttttacccg gccatggcaac cgtgggaagt ggagttaatg  600
aaacagctag ccaatcaggt cgcgatcgcc atccaacaat cggaattata tgagcaattg  660
cagctagctt tagaacggga aaaagaatta agccgcctaa aaactcgttt tttctccatg  720
gcttcccatg aatttcgtac tccccctcagt acggccttag ctgctgccca attactggaa  780
aattctgaag tggcctggct tgatcccgat aagcgtagcc ggaacttaca ccgtattcaa  840
aattccgtga aaaatatggt acagctcctg gatgatattt taatcattaa ccgtgccgaa  900
gcgggcaaat tggaatttaa tcctaattgg ttagatttga aattattgtt ccagcaattt  960
atcgaagaaa ttcaattaag tgtcagtgac caatattatt ttgactttat ttgtagcgct  1020
caagatacga aggcattggt ggatgaaagg ttagtgcagt ctatttttatc taatctgtta  1080
tctaatgcga ttaaatactc tcccgggggga gggcagatta aaattgccct aagcctagat  1140
tcggaacaga ttattttttga agtcaccgac cagggcattg gcatttcgcc agaggaccaa  1200
aagcaaattt ttgaacccctt tcatcgggggc aaaaatgtca gaaatattac gggaacagga  1260
ctcggtttaa tggttgccaa gaaatgtgtt gacttacaca gtggcagtat cttgctaaaa  1320
agtgcagttg accaggggaac aacagttact atctgtttaa aacgctataa ccatttgcct  1380
```

```
cgagcttag                                                                          1389

SEQ ID NO: 9              moltype = DNA   length = 828
FEATURE                   Location/Qualifiers
source                    1..828
                          mol_type = other DNA
                          organism = Synthetic construct SEQUENCE: 9
atgcgctggg tggaacagtt gcgcgaggcg ctgatcggcg acggcttcct gctgcattac    60
cagcccgtgc tcaacctgca gggcgagccg ctggagctgt atcaggcgtt cctgcggctg   120
gagcgcaatg gcgagatgat gtcgccgaat gcgttcatgg ccattgccga agaacacgac   180
ctgatcaccg agatcgaccg ctgggtggtg gcacgtgcca tccgccagct gggcgagcgc   240
cagcgcgccg ggcacaagac ccacctgctg gtgcgcatcg ggcccaattc gttctccgac   300
ccacagatga tcgacactat ccgcgaacag ctggcggtca acggcgtgcc aggagagcgg   360
ttgtggctgc agaccccgga atcgaaggta ttcacccacc tgcgcaacgc ccagcaattc   420
ctggcttcgg tctcggcaat gggctgcaag gtggggctgg agcaattcgg ttcgggactg   480
gattcgttcc agctgctcgc acacttccag cccgcgttcc tcaagctcga ccgcagcatc   540
accggcgaca tcgcctctgc ccgcgaaagc caggaaaaga tccgcgagat cacctcacgg   600
gcgcagccga ccggcatcct cacggtggcc gagttcgtgg ccgatgcaca gtcgatgagc   660
agcttcttca ctgcgggggt cgattacgtg caaggcgact tcgtcgcgcc caccggcccg   720
ctgatgggtg gcggtggttc aggtggaggg ggatccacat ctgaaaaacg cgatcacatg   780
gtcctgctgg agtatgtgac tgcggccggc atcacggatg catcttaa                828

SEQ ID NO: 10             moltype = DNA   length = 591
FEATURE                   Location/Qualifiers
source                    1..591
                          mol_type = unassigned DNA
                          organism = unidentified SEQUENCE: 10
atgcgcaagg gtgaagagct ctttaccggg gttgtgccta ttctcattga actggatggg    60
gatgtcaacg ggcacaaatt ttttgtgcgt ggagaaggag aaggcgatgc tacgattggg   120
aaactgtcac tgaagttcat ctgcaccacc ggcaaactgc ccgtcccttg cccacattg    180
gttacgacgc tgacctatgg cgtgcagtgt ttcagccggt acccggatca tatgaaacgt   240
catgactttt tcaaatccgc gatgccggaa ggttatgtgc aggaacgcac gatttacttc   300
aaagatgacg gaacgtataa aactcgtgca gaagttaaat tcgagggtga tactctggta   360
aatcgcattg aactcaaagg gatcgatttt aaagaagatg gaacattct ggggcacaaa    420
ctggaatata atttcaacag tcataaagta tatatcacgg ctgataaaca gaacaacggt   480
atcaaagcga attttaccat tcgtcataat gttgaagacg gaagtgtgca gctggctgat   540
cattatcagc aaaacacgcc gattgggat gggccggtac tgcttccatg a             591

SEQ ID NO: 11             moltype = DNA   length = 399
FEATURE                   Location/Qualifiers
source                    1..399
                          mol_type = other DNA
                          organism = Synthetic construct SEQUENCE: 11
atgtatacta tggatttacc agataaccat tatctctcga cgcagaccat ccttctgaag    60
gacttgaacg gtaccggtgt cggctcggga ggcggttcac agggcatcct cagcttggcg   120
ctgaaagata aagcggcact gtacagcgcc tacatgccgt ttgtcaaatc aggtggcatt   180
ttcgttccga cgccgaagcg ttacatgctt ggagatgagg tgtttttact gctgaccctt   240
cctgattcct ctgaacgctt gccggtggca gggaaagtaa tttggacgac tccggccggt   300
gctcagggta atcgtgcagc gggaatcggc gttcaatttc cggatggacc ggaaggcgaa   360
gccgtccgta ataaaattga gacgttactg gccggttga                          399

SEQ ID NO: 12             moltype = DNA   length = 723
FEATURE                   Location/Qualifiers
source                    1..723
                          mol_type = other DNA
                          organism = Synechocystis sp.

SEQUENCE: 12
atgagtgtca acttagcttc ccagttgcgg gaagggacga aaaaatccca ctccatggcg    60
gagaacgtcg gctttgtcaa atgcttcctc aagggcgttg tcgagaaaaa ttcctaccgt   120
aagctggttg gcaatctcta ctttgtctac agtgccatgg aagaggaaat ggcaaaattt   180
aaggaccatc ccatcctcag ccacatttac ttccccgaac tcaaccgcaa acaaagccta   240
gagcaagacc tgcaattcta ttacggctcc aactggcggc aagaagtgaa aatttctgcc   300
gctggccaag cctatgtgga ccgagtccgg caagtggccg ctacggcccc tgaattgttg   360
gtggcccatt cctacacccg ttacctgggg gatctttccg gcggtcaaat tctcaagaaa   420
attgcccaaa atgccatgaa tctccacgat ggtggcacag ctttctatga atttgccgac   480
attgatgacg aaaaggcttt taaaaatacc taccgtcaag ctatgaatga tctgcccatt   540
gaccaagcca ccgccgaacg gattgtggat gaagccaatg acgcctttgc catgaacatg   600
aaaatgttca cgaacttga aggcaacctg atcaaggcga tcggcattat ggtgttcaac    660
agcctcaccc gtcgccgcag tcaaggcagc accgaagttg gcctcgccac ctccgaaggc   720
tag                                                                  723

SEQ ID NO: 13             moltype = DNA   length = 705
FEATURE                   Location/Qualifiers
source                    1..705
                          mol_type = unassigned DNA
                          organism = unidentified
```

```
SEQUENCE: 13
gtgagcaagg gcgaggagga taacatggcc atcatcaagg agttcatgcg cttcaaggtg   60
cacatggagg gctccgtgaa cggccacgag ttcgagatcg agggcgaggg cgagggccgc  120
ccctacgagg gcacccagac cgccaagctg aaggtgacca agggtggccc cctgcccttc  180
gcctgggaca tcctgtcccc tcagttcatg tacggctcca aggcctacgt gaagcacccc  240
gccgacatcc ccgactactt gaagctgtcc ttccccgagg gcttcaagtg ggagcgcgtg  300
atgaacttcg aggacggcgg cgtggtgacc gtgacccagg actcctcct gcaggacggc  360
gagttcatct acaaggtgaa gctgcgcggc accaacttcc cctccgacgg ccccgtaatg  420
cagaagaaga ccatgggctg ggaggcctcc tccgagcgga tgtaccccga ggacggcgcc  480
ctgaagggcg agatcaagca gaggctgaag ctgaaggacg gcggccacta cgacgctgag  540
gtcaagacca cctacaaggc caagaagccc gtgcagctgc ccggcgccta caacgtcaac  600
atcaagttgg acatcacctc ccacaacgag gactacacca tcgtggaaca gtacgaacgc  660
gccgagggcc gccactccac cggcggcatg gacgagctgt acaag           705

SEQ ID NO: 14      moltype = DNA  length = 164
FEATURE            Location/Qualifiers
source             1..164
                   mol_type = other DNA
                   organism = Klebsiella pneumoniae
SEQUENCE: 14
tttaatggat cctgttcgct ggtgctatcg gcgtcaaaga atgctattta ttcgccgaca   60
aatatacatt tgttcacgtt tcattaagtt atataacaga taaccatcga ctattaataa  120
acagtcattg atagatgaaa acgccgccct acgggcttgc tctc            164

SEQ ID NO: 15      moltype = DNA  length = 705
FEATURE            Location/Qualifiers
source             1..705
                   mol_type = other DNA
                   organism = Klebsiella pneumoniae
SEQUENCE: 15
atgacagagg gaacgataaa gaccagtaag tatgaaatta ttgctatttt cagagaggag   60
ttgcgcaaac gtactgaaat tgaaatattt tttaacaaca ccagtatcat aacccaactg  120
acgcgcgtgg actttgccga gtttcatatt cagacccatc gcaaaatccc gtccgggcat  180
aaaattcgct ttctcctgca tagcgattca gggaaaatag agtttaatgc ggccctgaca  240
aaacatgaca atagcggtgt cgataaaggt atccgctacg cttttcatt gcctgaatgc  300
ctgcaggtag tgcagcgtcg ccgcgatccc cgctttcgtt tacgccatga gcatgacttt  360
tattgccgcg gccgccataa aaacggcgaa aactatcttt tcgatatcaa agacatttca  420
gatggcggtt gcgcattgat gaccaaaacg ccgaatctta aatttctcag ccacaacgcc  480
ttactgaaaa acgccgtact tatgcttgca gaatatggcg agatcaccat cgacctggtg  540
gtcaaaaatg tcattgttat caccctggat aacgctaatg aagagagtga gagctactat  600
cagatatcct gccagtttaa gttccgccat ctcgatgacc agcgcagaat agagaagata  660
ctgctggacc tgatcttaga agccaagcgc aaaaagagaa tctga          705

SEQ ID NO: 16      moltype = DNA  length = 717
FEATURE            Location/Qualifiers
source             1..717
                   mol_type = unassigned DNA
                   organism = unidentified
SEQUENCE: 16
tcatttgtag agttcatcca tgccgtgcgt gatacctgct gcagtaacga actccagcag   60
caccatgtgg tcgcgctttt cgttcgggtc tttggacagt ttagactggg tggacaggta  120
gtggttatcc ggcagcagaa ccggaccatc accgatcgga gtgttctgct ggtagtggtc  180
cgccagctgt acgctaccgt cttcaacgtt atggcgaatt ttgaagttag ctttgatacc  240
gttcttctgt ttgtctgcgg tgatgtaaac gttatgggag ttgaagttat attccagttt  300
gtggcccagg atgttgccgt cctctttgaa atcaatgcct ttcagttcaa tacggttcac  360
cagagtatca ccttcaaatt taacctctgc acgggttttg taggtgccat cgtctttgaa  420
agaaatggtg cgctcctgta cataaccttc cggcattgca gatttgaaga aatcatgctg  480
cttcatgtga tccgggtaac gagaaaaaca ctgaacacca taggtcaggg tagtcaccag  540
agtcggccac ggaaccggca gtttaccggt agtgcagatg aatttcaggg tcagtttacc  600
gttggttgca tcaccttcac cttcaccacg aacagagaat ttgtggccgt taacatcacc  660
atccagttca accaggatcg gaacaacacc ggtgaacagt tcttcacctt tactcat     717

SEQ ID NO: 17      moltype = DNA  length = 747
FEATURE            Location/Qualifiers
source             1..747
                   mol_type = other DNA
                   organism = Synechocystis sp.
SEQUENCE: 17
atggccgtca ctgatttaag tttgaccaat tcttccctga tgcctacgtt gaacccgatg   60
attcaacagt tggccctggc gatcgccgct agttggcaaa gtttacccct caagccctat  120
caattgccgg aggatttggg ctacgtagaa ggccgcctgg aaggggaaaa gttagtgatt  180
gaaaatcggt gctaccaaac gccccagttt cgcaaaatgc atttggagtt ggccaaggtg  240
ggcaaagggt tggatattct ccactgtgta atgtttcctg agcctttata cggtctacct  300
ttgtttggct gtgacattgt ggccggcccc ggtggagtaa gtgcggctat tgcggatcta  360
tcccccaccc aaagcgatcg ccaattgccc gcagcgtacc aaaaatcatt ggcagagcta  420
ggccagccag aatttgagca acaacgggaa ttgcccccct ggggagaaat attttctgaa  480
tattgttat tcatccgtcc cagcaatgtc actgaagaag aaagatttgt acaaggata  540
gtggactttt tgcaaattca ttgtcaccaa tccatcgttg ccgaacccct tgtctgaagct  600
caaactttgg agcaccgtca ggggcaaatt cattactgcc aacaacaaca gaaaaatgat  660
```

-continued

```
aaaacccgtc gggtactgga aaaagctttt ggggaagctt gggcggaacg gtatatgagc   720
caagtcttat ttgatgttat ccaataa                                        747

SEQ ID NO: 18          moltype = DNA   length = 534
FEATURE                Location/Qualifiers
source                 1..534
                       mol_type = other DNA
                       organism = Caulobacter sp.
SEQUENCE: 18
atgtccgatc agtctcaaga acctacaatg gaggaaatcc tcgcctccat tcgacgcatc    60
atctcggagg atgacgcgcc ggcggagcct gcggccgaag cggcgccccc gccgccgccg   120
gaacccgaac ctgaaccggt gtcgttcgac gacgaggttc tggaattgac ggatccgatc   180
gcgcccgagc ccgagctgcc gccgctggag actgtcggcg acatcgacgt ctattcgccg   240
ccggaacctg agtcggaacc ggcctacacg ccgccgccgg cggctccggt gtttgatcgc   300
gacgaagtcg ccgagcagct ggtcggcgtt tcggccgctt cggccgcggc gagcgccttc   360
ggcagcctga gctcggccct gctgatgccc aaggacggtc ggacgctgga agacgtcgta   420
cgcgagctgc tgcgcccgct gctcaaggag tggctggacc agaacctgcc gcgcatcgtc   480
gagaccaagg ttgaggaaga agtgcagcgt atctctcggg gacgcggcgc ctaa          534

SEQ ID NO: 19          moltype = DNA   length = 22
FEATURE                Location/Qualifiers
source                 1..22
                       mol_type = other DNA
                       organism = Synthetic construct
SEQUENCE: 19
ggttaattcc tcctgttagc cc                                              22

SEQ ID NO: 20          moltype = DNA   length = 1032
FEATURE                Location/Qualifiers
source                 1..1032
                       mol_type = other DNA
                       organism = Synechocystis sp.
SEQUENCE: 20
ttattctgcc agttgaaaat tgcccttacc aagacgtttg actttcatca actgattatc    60
tgcctgttct acccaatact ggagtgcttc accctggttg gtaaatacac tgactccccc   120
catactcaag ctgattgcca tgggtcccgc agatgtgggt actgggtttt gggcaatggt   180
ggcttgaatt ctttctagga gcacagcggt ctgctcccga ccagaaccag gcagaataag   240
catgaactca tctcctcccc atctgcccaa aatatcgtag gaacgaagaa ctgaaatgat   300
taaacgggca ctaccctgca gaacctcgtc tccgactaaa tgaccgtgtt gatcgttgat   360
ttgtttaaag ttgtcaaaat caatcatgac aatggaaata ggagaatttt tgcgggtagc   420
gtactcccat tcccgtttta gaagagtttc aatgcccaaa cggttccaga gtcttgttaa   480
gctatcgacc atggccaccc tttcaagttc atccagttct tgaattagct gtatttgagc   540
ctccgatagg gcgatcgcg ccagttcaga ctccaccatt ttggagaggt cgtagagaat   600
ttcctgttct tccgccgaca attcccgggg cacccgatca atggcgcaga gggttcccac   660
atggatatct tgacccaaat taaggggata accggcataa aatcggatga aaggctcgtc   720
ggttaccaag ggattgtcag caaagcgttc atcctgggta gcatcctcga ccaacagtaa   780
ttcatccctg aggatggcgt gggcgcaaaa ggcaatttca gggggggttt cggaagcatt   840
taacccttga atagatttaa accactggcg tgattcatca actattgata tggcggcaat   900
gggcactttg agggaccggc agaccatacg ggtaatacgc tcaaatcttt cttcaatggg   960
agtatccaaa atattgagtt gcctcaaaac tgccaggcgt tgctcctcat tttgcggtaa  1020
tttagcttcc at                                                       1032

SEQ ID NO: 21          moltype = DNA   length = 309
FEATURE                Location/Qualifiers
source                 1..309
                       mol_type = unassigned DNA
                       organism = unidentified
SEQUENCE: 21
ctatttgagg cgctaaatga aaccttaacg ctatggaact cgccgcccga ctgggctggc    60
gatgagcgaa atgtagtgct tacgttgtcc cgcatttggt acagcgcagt aaccggcaaa   120
atcgcgccga aggatgtcgc tgccgactgg gcaatggagc gcctgccggc ccagtatcag   180
cccgtcatac ttgaagctag acaggcttat cttggacaag aagaagatcg cttggcctcg   240
cgcgcagatc agttggaaga atttgtccac tacgtgaaag gcgagatcac caaggtagtc   300
ggcaaataa                                                            309

SEQ ID NO: 22          moltype = DNA   length = 23
FEATURE                Location/Qualifiers
source                 1..23
                       mol_type = other DNA
                       organism = Synthetic construct
SEQUENCE: 22
ggaattgtga gcggataaca att                                            23

SEQ ID NO: 23          moltype = DNA   length = 803
FEATURE                Location/Qualifiers
source                 1..803
                       mol_type = other DNA
                       organism = Synthetic construct
SEQUENCE: 23
```

```
agacccactt tcacatttaa gttgttttc taatccgcat atgatcaatt caaggccgaa      60
taagaaggct ggctctgcac cttggtgatc aaataattcg atagcttgtc gtaataatgg     120
cggcatacta tcagtagtag gtgtttccct ttcttcttta gcgacttgat gctcttgatc     180
ttccaatacg caacctaaag taaaatgccc cacagcgctg agtgcatata atgcattctc     240
tagtgaaaaa ccttgttggc ataaaaaggc taattgattt tcgagagttt catactgttt     300
ttctgtaggc cgtgtaccta aatgtacttt tgctccatcg cgatgactta gtaaagcaca     360
tctaaaactt ttagcgttat tacgtaaaaa atcttgccag ctttcccctt ctaaagggca     420
aaagtgagta tggtgcctat ctaacatctc aatggctaag gcgtcgagca aagcccgctt     480
atttttaca tgccaataca atgtaggctg ctctacacct agcttctggg cgagtttacg      540
ggttgttaaa ccttcgattc cgacctcatt aagcagctct aatgcgctgt taatcacttt     600
acttttatct aatctagaca tcattaattc ctcctttttg ttgacattat atcattgata     660
gagttatttg tcaaactagt tttttatttg gatccctcg agttcatgaa aaactaaaaa      720
aaatattgac actctatcat tgatagagta taattaaaat aagctttgat ggtaccgtta     780
acagatctga aggagatata cat                                             803
```

```
SEQ ID NO: 24              moltype = DNA  length = 1377
FEATURE                    Location/Qualifiers
source                     1..1377
                           mol_type = other DNA
                           organism = Acinetobacter baylyi
SEQUENCE: 24
ttaattggct gttttaatat cttcctgctt tgcaattacg ccttcaaata gttgaatttc      60
ttcttctaaa tgtgtcagta aattctgcat tcttggcaat gcattacggc atgcaatcaa     120
accaacttca agtttatcta aataactggt cattgtaata ttcaatgctt gaccgtctaa     180
tacaattgaa gctgggtaga gtgcatcaag tttggcacca ttccagtaaa gtggctctct     240
tgggccaggc acattggaaa taaccagatt gaaggcttgg cgttttggca tcatgccaga     300
aattatgttg agtcctgcag ggccatatac gacagcacta taatttagaa tctgatcgct     360
ggtcatacgt ttgaagcgtt gctttgagtt ttgaacacta cggcggataa tttcaagacg     420
ttgtaaagga tcatctttgt gggttgccaa atttgccaga atcatcgtaa tacggttgct     480
gacatctgaa tcgtcattgc gaatagaggc tggaaccatg gcaattaatg gttttgaagg     540
caaactatta tgactcatca aatacgcacg taatgcacca gaacataccg ctagtacaac     600
atcattaatg gtcacattca acgatttggc aatattacga aaacgatcta ggtcaaaaga     660
ctgtgctgca aaacgtcgcg atgagctcac acgctgattc aaaatagaac aaggcgcctg     720
aaagcttgaa acatgatcag gattacgtcc aatatcttta aatactgtct gagaaagctc     780
ttgaatgact gtgggtgtcg cctgaagctg actcttaata ccagacatga tttcttaat     840
tttacctgtt ttaggttctc ttaagcgctt tgcacgtttt ccctcaacac accaaggtgg     900
cacgatactt ttttctgtta catcatggga gagtgatttt tcaattaacc gcataccagc     960
aacgccatcg accatcgcat ggtgaatttt gaagtacatg gcaaaacgat tgccttcaat    1020
tccttcaata atattgcagg tccacaaggg ctttgcccga tctaccagcg tactgtgctc    1080
ttgtgaaata taaataagca attcacgaat acgaccagga tgaggcagtg caatatgacg    1140
aaaatgatga tctaaatcaa actcttcatc ttcatcccaa aaaagcccat tcagtttatt    1200
gttgaatggt ggaacaggga ttgattttga tatccggata tcattcacca gatcttgaat    1260
aaaggtgtct ggggcgttat caggaatctg aaacaaaaat aaaccaccta catgcatagg    1320
ctgttgtctt ttttctagtg acaggaatat aaaatcaatc ggatgtaatg ggcgcat       1377
```

```
SEQ ID NO: 25              moltype = DNA  length = 765
FEATURE                    Location/Qualifiers
source                     1..765
                           mol_type = other DNA
                           organism = Escherichia coli
SEQUENCE: 25
atgataaggc aggttatcca gcgaataagc aaccctgaag caagcatcga gagcttgcag      60
gaacggcgtt tttggttgca gtgtgagcgt gcttacacct ggcagccgat ctatcaaaca     120
tgcgggcggt taatggccgt ggagctatta acggtggtca cgcatccctt gaacccttcg     180
caacgcctgc cgccggatcg ctattttact gaaatcaccg tcagccatcg gatggaggtt     240
gtgaaagagc agattgattt gctggcgcaa aaagccgact tctttatgga gcacggcctg     300
ctggcatcgg tcaatattga tggccctacg ctcatcgccc tgcgtcagca accaaaaatc     360
ctgcgccaga ttgagcgtct tccctggctg cgtttcgaac tggtggagca tatccgtctg     420
ccgaaagatt caacctttgc ctcgatgtgt gaatttggcc cgctgtggct ggatgatttt     480
ggtaccggga tggcaaattt ctctgcgcta agtgaagtgc gttatgacta catcaaaatc     540
gcgcgagaac tgtttgtgat gctgcgtcag tcgccggaag gacgcacact cttttctcag     600
cttttacatc taatgaatcg ctattgtcgc ggggtgattg tcgagggcgt agaaacgccg     660
gaagagtggc gtgatgttca gaactcgccc gcattcgccg cacaaggctg gtttctttca     720
cgcccggcac cgatagaaac gctgaatacg gcggttctgc gcta                      765
```

```
SEQ ID NO: 26              moltype = DNA  length = 888
FEATURE                    Location/Qualifiers
source                     1..888
                           mol_type = other DNA
                           organism = Escherichia coli
SEQUENCE: 26
atgcttatct tattaggtta cctggttgtt ctcggtacag ttttcggcgg ttatttgatg      60
accggtggaa gccttggagc actctatcaa cccgctgaac tggtgattat tgccggtgca     120
gggattgggt cgtttatcgt cggcaataat ggcaaagcga ttaaaggcac gctgaaggcg     180
ctgccgttgc tgtttcgtcg ctccaaatac accaaaagcaa tgtatatgga tctgctggct     240
ctgctttatc ggttgatggc gaaatcgcgg cagatgggga tgtttcgct ggaacgtgat      300
attgaaaatc cccgtgagag cgagatcttc gccagctacc cacgcatcct cgcggatagc     360
gtcatgcttg atttttatcgt cgattatctg cgcctgatta tcagcggtca catgaacacc     420
ttcgaaatcg aagctctgat ggatgaagag attgagacgc acgaaagcga ggcagaagtc     480
```

```
ccggcgaaca gtctggcgct ggtcggggac tcacttccgg cgtttggtat tgttgcggct   540
gtaatggggg tcgttcacgc gttaggttca gccgatcgtc ctgccgccga gctgggtgcg   600
cttatcgcac atgcgatggt ggggactttc ctcggcattt tattggctta cggatttatt   660
tccccattag cgactgtttt acgtcagaaa agcgccgaaa ccagcaaaat gatgcagtgc   720
gtcaaagtca ctctgctttc taatctgaac ggttacgcac cgcctatcgc cgttgagttt   780
ggtcgcaaaa cgctctattc cagcgaacgt ccgtcgttta ttgaactgga agagcatgtg   840
cgtgcggtga aaaatccgca acaacagacg acaaccgagg aagcatga                888
```

```
SEQ ID NO: 27          moltype = DNA   length = 927
FEATURE                Location/Qualifiers
source                 1..927
                       mol_type = other DNA
                       organism = Escherichia coli
SEQUENCE: 27
atgaagaatc aagcgcatcc gattattgtc gtcaaacgac gcaaagccaa aagccacggg   60
gcagcacatg gatcgtggaa gattgcttat gccgacttta tgactgcgat gatggccttt  120
tttctggtga tgtggctgat ctccatctcc agcccaaaag agctgattca gattgcggag  180
tacttccgga ctccactggc gactgcggtt acgggcggcg atcgcatttc taatagtgaa  240
agcccaattc ccggcggtgg tgatgattac acccaaagcc aggggggaagt gaataagcag  300
ccgaacatcg aagagctgaa aaaacgcatg gagcaaagtc gattgcggaa attgcggggt  360
gatctcgacc agttgataga gtccgatccg aaactgcggg cgttacgtcc ccatctcaaa  420
atcgatctgg tccaggaagg tctacgtatt cagatcatcg atagccagaa tcgcccgatg  480
tttagaaccg gcagtgccga tgtcgaaccc tatatgcgcg acattctgcg cgccattgcg  540
cctgtactga acggtattcc caaccgtatt agcctttcag gtcataccga tgatttcccc  600
tacgccagcg gtgagaaagg atatagcaac tgggagcttt ctgccgatcg ggccaatgca  660
tcccgccagc aactgatggt cggagggttg gatagcggca aagtgttacg tgtcgtcaac  720
atggcggcaa cgatgcgctt aagcgatcgc ggacctgatg atgccgtcaa ccgtcgcatc  780
agcctgctgg tactgaacaa acaagccgaa caggccattt tgcatgaaaa cgccgaaagc  840
cagaatgagc cagtaagcgc cctggaaaaa cctgaggttg caccacaggt cagtgttccc  900
acaatgccat cagccgaacc gaggtga                                       927
```

```
SEQ ID NO: 28          moltype = DNA   length = 2067
FEATURE                Location/Qualifiers
source                 1..2067
                       mol_type = other DNA
                       organism = Synthetic construct
SEQUENCE: 28
atgataaggc aggttatcca gcgaataagc aaccctgaag caagcatcga gagcttgcag   60
gaacggcgtt tttggttgca gtgtgagcgt gcttacacct ggcagccgat ctatcaaaca  120
tgcgggcggt taatggccgt ggagctatta acggtggtca cgcatccctt gaacccttcg  180
caacgcctgc cgccggatcg ctattttact gaaatcaccg tcagccatcg gatgtgaggtt  240
gtgaaagagc agattgattt gctggcgcaa aaagccgact tctttataga gcacggcctg  300
ctggcatcgg tcaatattga tggccctacg ctcatcgccc tcgtcagca accaaaaatc  360
ctgcgccaga ttgagcgtct tccctggctg cgtttcgaac tggtggagca tatccgtctg  420
ccgaaagatt caacctttgc ctcgatgtgt gaatttggcc cgctgtggct ggatgattt  480
ggtaccggga tggcaaattt ctctgcgcta agtgaagtgc gttatgacta catcaaaatc  540
gcgcgagaac tgtttgtgat gctgcgtcag tcgccggaag gacgcacact cttttctcag  600
cttttacatc taatgaatcg ctattgtcgc ggggtgattg tcgagggcgt agaaacgccg  660
gaagagtggc gtgatgttca gaactcgccc gcattcgccg cacaaggctg gtttctttca  720
cgcccggcac cgatagaaac gctgaatacg gcggttctgg cgctaggagg cagcgcgggt  780
tctgctgcgg gttccggcgc cgtgagcaag ggcgaggagg ataacatggc catcatcaag  840
gagttcatgc gcttcaaggt gcacatggag ggctccgtga acggccacga gttcgagatc  900
gagggcgagg cgagggccg ccctacgag ggcacccaga ccgccaagct gaaggtgacc  960
aagggtggcc cctgcccctt cgcctgggac atcctgtccc ctcagttcat gtacggctcc  1020
aaggcctacg tgaagcaccc cgccgacatc cccgactact tgaagctgtc cttcccggag  1080
ggcttcaagt gggagcgcgt gatgaacttc gaggacggcg gcgtggtgac cgtgacccag  1140
gactcctccc tgcaggacgg cgagttcatc tacaaggtga agctgcgcgg caccaacttc  1200
ccctccgacg gccccgtaat gcagaagaag accatgggct gggaggcctc ctccgagcgg  1260
atgtaccccg aggacggcgc cctgaaaggc gagatcaagc agaggctgaa gctgaaggac  1320
ggcggccact acgacgctga ggtcaagacc acctacaagg ccaagaagcc cgtgcagctg  1380
cccggcgcct acaacgtcaa catcaagttg gacatcacct cccacaacga ggactacacc  1440
atcgtggaac agtacgaacg cgccgagggc cgccactcca ccggcggcat ggacgagctg  1500
tacaagcctg caggcgcctt aattaatatg catatgtccg atcagtctca agaacctaca  1560
atggaggaaa tcctcgcctc cattcgacgc atcatctcgg agatgacgc gccggcggag  1620
cctgcggccg aagcggcgcc cccgccgccg ccggaacccg aacctgaacc ggtgtcgttc  1680
gacgacgagg ttctggaatt gacggatccg atcgcgcccg agcccgagct gccgccgctg  1740
gagactgtcg gcgacatcga cgtctattcg ccgccggaac ctgagtcgga accggcctac  1800
acgccgcgc cggcggctcc ggtgtttgat cgcgacgaag tcgccgagca gctggtcggc  1860
gtttcggccg cttcggcccg ggcgagcgcc ttcggcgacc tgagctcggc cctgctgatg  1920
cccaaggacg gtcggacgct ggaagacgtc gtacgcgagc tgctgcgccc gctgctcaag  1980
gagtggctgg accagaacct gccgcgcatc gtcgagacca aggttgagga agaagtgcag  2040
cgtatctctc ggggacgcgg cgcctaa                                       2067
```

```
SEQ ID NO: 29          moltype = DNA   length = 2179
FEATURE                Location/Qualifiers
source                 1..2179
                       mol_type = other DNA
                       organism = Synthetic construct
SEQUENCE: 29
```

```
atgacagagg gaacgataaa gaccagtaag tatgaaatta ttgctatttt cagagaggag   60
ttgcgcaaac gtactgaaat tgaaatattt tttaacaaca ccagtatcat aacccaactg  120
acgcgcgtgg actttgccga gtttcatatt cagacccatc gcaaaatccc gtccgggcat  180
aaaattcgct ttctcctgca tagcgattca gggaaaatag agtttaatgc ggccctgaca  240
aaacatgaca atagcggtgt cgataaaggt atccgctacg cttttcatt gcctgaatgc   300
ctgcaggtag tgcagcgtcg ccgcgatccc cgctttcgtt tacgccatga gcatgacttt  360
tattgccgcg gccgccataa aaacggcgaa aactatcttt tcgatatcaa agacatttca  420
gatggcggtt gcgcattgat gaccaaaacg ccgaatctta aatttctcag ccacaacgcc  480
ttactgaaaa acgccgtact tatgcttgca gaatatggcg agatcaccat cgacctggtg  540
gtcaaaaatg tcattgttat caccctggat aacgctaatg aagagagtga gagctactat  600
cagatatcct gccagtttaa gttccgccat ctcgatgacc agcgcagaat agagaagata  660
ctgctggacc tgatcttaga agccaagcgc aaaaagagaa tctgagctca agctttctag  720
aacaaaaact catctcagaa gaggatctga atagcgccgt cgaccatcat catcatcatc  780
attgagttta aacggtctcc agcttggctg ttttggcgga tgagagaaga ttttcagcct  840
gatacagatt aaatcagaac gcagaagcgg tctgataaaa cagaatttgc ctggcggcag  900
tagcgcggtg gtcccacctg accccatgcc gaactcagaa gtgaaacgcc gtagcgccga  960
tggtagtgtg gggtctcccc atgcgagagt agggaactgc caggcatcaa ataaaacgaa 1020
aggctcagtc gaaagactgg gcctttcgtt ttatctgttg tttgtcggtg aacgctctcc 1080
tgagtaggac aaatccgccg ggagcggatt tgaacgttgc gaagcaacgg cccggagggt 1140
ggcgggcagg acgcccgcca taaactgcca ggcatcaaat taagcagaag gccatcctga 1200
cggatggcct ttttgcggct agcatgactg gtggacagca aatgggtcgg gatctgtacg 1260
acgatgacga taaggatcga tggggatccg agctcgagtc atttgtagag ttcatccatg 1320
ccgtgcgtga tacctgctgc agtaacgaac tccagcagca ccatgtggtc gcgcttttcg 1380
ttcgggtctt tggacagttt agactgggtg gacaggtagt ggttatccgg cagcagaacc 1440
ggaccatcac cgatcggagt gttctgctgg tagtggtccg ccagctgtac gctaccgtct 1500
tcaacgttat ggcgaatttt gaagttagct ttgataccgt tcttctgttt gtctgccgtg 1560
atgtaaacgt tatgggagtt gaagttatat tccagtttgt ggcccaggat gttgccgtcc 1620
tctttgaaat caatgccttt cagttcaata cggttcacca gagtatcacc ttcaaattta 1680
acctctgcac gggtttttgta ggtgccatcg tctttgaaag aaatggtgcg ctcctgtaca 1740
taaccttccg gcattgcaga tttgaagaaa tcatgctgct tcatgtgatc cgggtaacga 1800
gaaaaacact gaacaccata ggtcagggta gtcaccagag tcggccacgg aaccggcagt 1860
ttaccggtag tgcagatgaa tttcagggtc agtttaccgt tggttgcatc accttcacct 1920
tcaccacgaa cagagaattt gtggccgtta acatcaccat ccagttcaac caggatcgga 1980
acaacaccgg tgaacagttc ttcacctttta ctcattttaa tggatcctgt tcgctggtgc 2040
tatcggcgtc aaagaatgct atttattcgc cgacaaatat acatttgttc acgtttcatt 2100
aagttatata acagataacc atcgactatt aataaacagt cattgataga tgaaaacgcc 2160
gccctacggg cttgctctc                                             2179
```

```
SEQ ID NO: 30          moltype = DNA   length = 2962
FEATURE                Location/Qualifiers
source                 1..2962
                       mol_type = other DNA
                       organism = Synthetic construct
SEQUENCE: 30
ttaattggct gttttaatat cttcctgctt tgcaattacg ccttcaaata gttgaatttc   60
ttcttctaaa tgtgtcagta aattctgcat tcttggcaat gcattacggc atgcaatcaa  120
accaacttca agtttatcta aataactggt cattgtaata ttcaatgctt gaccgtctaa  180
tacaattgaa gctgggtaga gtgcatcaag tttggcacca ttccagtaaa gtggctctct  240
tgggccaggc acattggaaa taaccagatt gaaggcttgg cgtttttggca tcatgccaga  300
aattatgttg agtcctgcag ggccatatac gacagcacta taatttagaa tctgatcgct  360
ggtcatcagt ttgaagcgtt gctttgagtt ttgaacacta cggcggataa tttcaagacg  420
ttgtaaagga tcatctttgt gggttgccaa atttgccaga atcatcgtaa tacggttgct  480
gacatctgaa tcgtcattgc gaatagaggc tggaaccatg gcaattaatg gttttgaagg  540
caaactatta tgactcatca aatacgcacg taatgcacca gaacataccg ctagtacaac  600
atcattaatg gtcacattca acgatttggc aatattacga aaacgatcta ggtcaaaaga  660
ctgtgctgca aaacgtcgcg atgagctcac acgctgattc aaaatagaac aaggcgcctg  720
aaagcttgaa acatgatcag gattacgtcc aatatctttta aatactgtct gagaaagctc  780
ttgaatgact gtgggtgtcg cctgaagctg actcttaata ccagacatga ttttcttaat  840
tttacctgtt ttaggttctc ttaagcgctt tgcacgtttt ccctcaacac accaaggtgg  900
cacgatactt ttttctgtta catcatggga gagtgatttt tcaattaacc gcataccagc  960
aacgccatcg accatcgcat ggtgaatttt gaagtacatg gcaaaacgat tgccttcaat 1020
tccttcaata atattgcagg tccacaaggg ctttgcccga tctagcagcg tactgtgctc 1080
ttgtgaaata taaataagca attcacgaat acgaccagga tgaggcagtg caatatgacg 1140
aaaatgatga tctaaatcaa actcttcatc ttcatcccaa aaaagcccat tcagtttatt 1200
gttgaatggt ggaacaggga ttgattttga tatccggata tcattcacca gatcttgaat 1260
aaaggtgtct ggggcgttat caggaatctg aaacaaaaat aaaccaccta catgcatagg 1320
ctgttgtctt ttttctagtg acaggaatat aaaatcaatc ggatgtaatg ggcgcattgg 1380
atacctcctt gaattctttc tcgagctcgg atccccatcg atccttatcg tcatcgtcgt 1440
acagatcccg acccatttgc tgtccaccag tcatgctacg ttagttcagg acgtgctcaa 1500
ctaccccagg aaagtgagtt tttaagaaat agtcttccca gttgatagcg cgaggatcaa 1560
aatagaacat gtcagcctct acgatcgatt ccttggcagc aatacgtaac ttctcagtat 1620
tcatgtcgtc aaagatacct tggaagaaca agtaaggctt gtagatgtca accagacgta 1680
acagcaagcg cgttttacgc ttcaagtcca tgtacttccc tttgaaccac tgacaaaaga 1740
tggtgtttgc aatctctaac accttcagag gcagtaagaa attcaaagtc aagtataagt 1800
gaaaggtact aaagcttgag aacaccatag cgcgaccaac atgcacgggg ttacgatcgg 1860
gattgatcca aggattcttc gtgaaatagc ggtgtgccat ttccggcagc gcggacagtt 1920
tcatgggggtt agcagcgctg gaccccacgt ggtacgtaac tggttccaca taacgctggt 1980
tagcatcgcg taccatcgca acaatcgtcg cattcacaac catatccgcc ggaatcagat 2040
cgataatagt cgacggacca cacaacatgc agcgaaggcg accttttcca tagtataccg 2100
```

```
gaacattatc gatggtgcgt acgccttcaa cccatcctgg aaagggttcc ttaaacgtac   2160
tggtgataat agtggggcga ataattgtca aagggatgtc tcccttgtac tgcatcaaca   2220
acatctcacc cagcgctttt gtgaagacat aaacattagg ccacccccaa tgacgagcac   2280
gctcgatccc catatccttc atagtgcttt taatggactt ctccgtagcc cctgcggctt   2340
gaagttcatt gattttagct tcgactaact ttttctccac gttaatatcc aaaccaaggc   2400
ggccattcaa tgactccccc atgtagtacg gcttttctaa aatcagcccg ttcttttcgc   2460
cggatacata tgctgtgctt acatgaacaa aaatcttcag cttgttacat tttttggcaa   2520
aatctaagac gtatttagcc ccatatgtat taataagcag ggatacatcg taacgctcaa   2580
taaaattgat ggtagcggct aagttcacca caacgtcaat ttcgcgccac atttcttcct   2640
ttaagttcac atctttaagg cacaagtctt cgcccgtgat gtctcccggc acgactgtta   2700
cttttttcgct tacgaaactg taaaaattgg cacccaagtt ttgcttaagt accttgaaca   2760
attccttgcc aaacacttcg ttctgtaaac gcagggcagc cgtttcatcg tctgtcgcac   2820
gcaataataa gtacaatttc ttaacattcg gttgcgaacg caacactttt tccacgaaga   2880
tcttggcaag ggagccggta gccctgtga caaggatcgc cttgttatcc agaaactcaa   2940
ggatggaacc catctcttcc at                                             2962

SEQ ID NO: 31            moltype = DNA  length = 3220
FEATURE                  Location/Qualifiers
source                   1..3220
                         mol_type = other DNA
                         organism = Synthetic construct
SEQUENCE: 31
atgagaattc ttttagtgga ggatgatttg ccgctggcgg aaacccttgc tgaagcattg   60
agtgaccagc tttacaccgt tgatattgcc accgacgctt ccctcgcctg ggactatgcc   120
tcccgactgg aatatgacct cgttattttg gatgtgatgc tgccggagtt ggacgggatt   180
accctctgtc aaaaatggcg atcgcacagt tatttaatgc caattttgat gatgacagcc   240
agggatacga tcaatgataa aatcacgggc ttggatgcgg gggcggatga ttatgtggtc   300
aagccagtgg atttgggga gttatttgcc agggtgcgag ctttgttgcg tcggggttgt   360
gcaacgtgcc aaccagtttt agagtggggg ccaatcaggt tggatccaag cacctatgaa   420
gttagttatg acaatgaggt tttgtctttg acccgcaagg aatacagcat tctggaatta   480
ctactccgca atggccgtcg ggtgctaagt cggagcatga ttatcgatag tatctcggaag   540
ttggagagtc ccccagagga agatacggtt aaggtgcatg tgcggagttt gcgacaaaaa   600
ttaaaaagtg ccggtttatc agcagatgcc attgaaacgg tccatggcat tgggtatcgt   660
ctggccaatt taacggaaaa atctttgtgc caagggaaca actagtaata atctagacca   720
ggcatcaaat aaaacgaaag gctcagtcga aagactgggc ctttcgtttt atctgttgtt   780
tgtcggtgaa cgctctctac tagagtcaca ctggctcacc ttcgggtggg cctttctgcg   840
tttatagtaa atcactgcat aattcgtgtc gctcaaggcg cactcccgtt ctggataatg   900
tttttttgcgc cgacatcata acggttctgg caaatattct gaaatgagct ggttagctag   960
tcaagcccat tgtgcttttc tctatcaacc tcagcttacc tgaaggggtg aacaggtctg   1020
ggttaattca tgttgcgaaa tgtaacagtt ttagtcgcat cagctaactt tccgatttct   1080
ttacgatttt ctcccccttt tcttcaattt tactttgtta ggatcgcatt tttaaaaaga   1140
ggagaaatac tagatgataa ggcaggttat ccagcgaata agcaaccctg aagcaagcat   1200
cgagagcttg caggaacggc gttttttggtt gcagtgtgag cgtgcttaca cctggcagcc   1260
gatctatcaa acatgcgggc ggttaatggc cgtggagcta ttaacggtgg tcacgcatcc   1320
cttgaaccct tcgcaacgcc tgccgccgga tcgctatttt actgaaatca ccgtcagcca   1380
tcggatggag gttgtgaaag agcagattga tttgctggcg caaaaagccg acttcttat   1440
agagcacggc ctgctggcat cggtcaatat tgatggccct agcgctcatcg ccctgcgtca   1500
gcaaccaaaa atcctgcgcc agattgagc tcttccctgg ctgcgtttcg aactggtgga   1560
gcatatccgt ctgccgaaag attcaacctt tgcctcgatg tgtgaatttg gccgctgtg   1620
gctggatgat tttggtaccg ggatggcaaa tttctctgcg ctaagtgaag tgcgttatga   1680
ctacatcaaa atcgcgcgag aactgtttgt gatgctgcgt cagtcgccgg aaggacgcac   1740
actcttttct cagcttttac atctaatgaa tcgctattgt cgcggggtga ttgtcgaggg   1800
cgtagaaacg ccggaagagt ggcgtgatgt tcagaactcg cccgcattcg ccgcacaagg   1860
ctggtttctt tcacgcccgg caccgataga aacgctgaat acggcggttc tggcgctagg   1920
aggcagcgcg ggttctgctg cgggttccgg cgccgtgagc aaaggcgagg aggataaacat   1980
ggccatcatc aaggagttca tgcgcttcaa ggtgcacatg gagggctccg tgaacggcca   2040
cgagttcgag atcgagggcg agggcgaggg ccgcccctac gagggcaccc agaccgccaa   2100
gctgaaggtg accaagggtg gccccctgcc cttcgcctgg gacatcctgt cccctcagtt   2160
catgtacggc tccaaggcct acgtgaagca ccccgccgac atccccgact acttgaagct   2220
gtccttcccc gagggcttca gtgggagcg cgtgatgaac ttcgaggacg gcggcgtggt   2280
gaccgtgacc caggactcct ccctgcagga cggcgagttc atctacaagg tgaagctgcg   2340
cggcaccaac ttcccctccg acggccccgt aatgcagaag aagaccatgg ctgggaggc   2400
ctcctccgag cggatgtacc ccgaggacg cgccctgaag ggcgagatca gcagaggct   2460
gaagctgaag gacggcggcc actacgacgc tgaggtcaag accacctaca aggccaagaa   2520
gcccgtgcag ctgccggcg cctacaacgt caacatcaag ttggacatca cctcccacaa   2580
cgaggactac accatcgtgg aacagtacga acgcgccgag ggcgccact ccaccggcgg   2640
catggacgag ctgtacaagc ctgcaggcgc cttaattaat atgcatatgt ccgatcagtc   2700
tcaagaacct acaattggagg aaatcctcgc ctccattcga cgcatcatct cggaggatga   2760
cgcgccggcg gagcctgcgg ccgaagcggc gcccccgccg cgccggaac cggaacctga   2820
accggtgtcg ttcgacgacg aggttctgga attgacggat ccgatcgcgc ccgagcccga   2880
gctgccgccg ctggagactg tcggcgacat cgacgtctat tcgccgccgg aacctgagtc   2940
ggaaccggcc tacacgccgc cgccggcggc tccggtgttt gatcgcgacg aagtcgccga   3000
gcagctggtc ggcgtttcgg ccgcttcggc cgcggcgagc gccttcggca gcctgagctc   3060
ggccctgctg atgcccaagg acgtcggac gctggaagac gcgtacgcg agctgctgcg   3120
cccgctgctc aaggagtggc tggaccagaa cctgccgcgc atcgtcgaga ccaaggttga   3180
ggaagaagtg cagcgtatct ctcgggggacg cggcgcctaa                        3220

SEQ ID NO: 32            moltype = DNA  length = 1952
FEATURE                  Location/Qualifiers
```

-continued

```
source              1..1952
                    mol_type = other DNA
                    organism = Synthetic construct
SEQUENCE: 32
atgcgctggg tggaacagtt gcgcgaggcg ctgatcggcg acggcttcct gctgcattac  60
cagcccgtgc tcaacctgca gggcgagccg ctggagctgt atcaggcgtt cctgcggctg  120
gagcgcaatg gcgagatgat gtcgccgaat gcgttcatgg ccattgccga agaacacgac  180
ctgatcaccg agatcgaccg ctgggtggtg gcacgtgcca tccgccagct gggcgagcgc  240
cagcgcgccg ggcacaagac ccacctgctg gtgcgcatcg ggcccaattc gttctccgac  300
ccacagatga tcgacactat ccgcgaacag ctggcggtct acggcgtgcc aggagagcgg  360
ttgtggctgc agaccccgga atcgaaggta ttcacccacc tgcgcaacgc ccagcaattc  420
ctggcttcgg tctcggcaat gggctgcaag gtggggctgg agcaattcgg ttcgggactg  480
gattcgttcc agctgctcgc acacttccag cccgcgttcc tcaagctcga ccgcagcatc  540
accggcgaca tcgcctctgc ccgcgaaagc caggaaaaga tccgcgagat cacctcacgg  600
gcgcagccga ccggcatcct cacggtggcc gagttcgtgg ccgatgcaca gtcgatgagc  660
agcttcttca ctgcgggggt cgattacgtg caaggcgact tcgtcgcgcc caccggcccg  720
ctgatgggtg gcggtggttc aggtggaggg ggatccacat ctgaaaaacg cgatcacatg  780
gtcctgctgg agtatgtgac tgcggccggc atcacggatg catcttaagg ataaatatgt  840
atactatgga tttaccagat aaccattatc tctcgacgca gaccatcctt ctgaaggact  900
tgaacggtac cggtgtcggc tcgggaggcg gttcacaggg catcctcagc ttggcgctga  960
aagataaagc ggcactgtac agcgcctaca tgccgtttgt caaatcaggt ggcattttcg  1020
ttccgacgcc gaagcgttac atgcttggag atgaggtgtt tttactgctg acccttcctg  1080
attcctctga acgcttgccg gtggcaggga aagtagtttg gacgactccg gccggtgctc  1140
agggtaatcg tgcagcggga atcggcgttc aatttccgga tggaccggaa ggcgaagccg  1200
tccgtaataa aattgagacg ttactggccg gttgaccgtg gccaggaccc aacgctgccc  1260
gagatctcga tcccgcgaaa ttaatacgac tcactatagg gagaccacaa cggtttccct  1320
ctagaaataa ttttgtttaa ctttaagaag gagatataca tatgcgcaag ggtgaagagc  1380
tctttaccgg ggttgtgcct attctcattg aactggatgg ggatgtcaac gggcacaaat  1440
tttttgtgcg tggagaagga gaaggcgatg ctacgattgg gaaactgtca ctgaagttca  1500
tctgcaccac cggcaaactg cccgtccctt ggcccacatt ggttacgacg ctgacctatg  1560
gcgtgcagtg tttcagccgg tacccggatc atatgaaacg tcatgacttt ttcaaatccg  1620
cgatgccgga aggttatgtg caggaacgca cgatttactt caaagatgac ggaacgtata  1680
aaactcgtgc agaagttaaa ttcgagggtg atactctggt aaatcgcatt gaactcaaag  1740
ggatcgattt taaagaagat gggaacattc tggggcacaa actggaatat aatttcaaca  1800
gtcataaagt atatatcacg gctgataaac agaacaacgg tatcaaagcg aattttacca  1860
ttcgtcataa tgttgaagac ggaagtgtgc agctggctga tcattatcag caaaacacgc  1920
cgattgggga tgggccggta ctgcttccat ga                                1952
```

MICROBIAL STEM CELL TECHNOLOGY

CROSS-REFERENCE TO RELATED APPLICATIONS

This application is a divisional of U.S. patent application Ser. No. 16/393,671, filed Apr. 24, 2019 (now U.S. Pat. No. 11,525,117) which claims priority to U.S. Provisional Application Ser. No. 62/712,857, filed Jul. 31, 2018, and U.S. Provisional Application Ser. No. 62/661,818, filed Apr. 24, 2018, which are herein incorporated by reference in their entirety.

GOVERNMENT RIGHTS

This invention was made with government support under grant No. GM118792 awarded by the National Institutes of Health. The government has certain rights in the invention.

REFERENCE TO A SEQUENCE LISTING

This application contains references to nucleic acid sequences which have been submitted as the sequence listing XML file entitled "Seq.IDNos.1-32", file size 59 KiloBytes (KB), created Apr. 21, 2023, which is hereby incorporated by reference in its entirety.

BACKGROUND

Field

Embodiments of the present disclosure generally relate to microbial stem cell technology.

Description of the Related Art

Fermentation-based chemical production processes utilize batch microbial cultures to produce a variety of valuable biosynthetic products ranging from pharmaceuticals to biofuels. Such bioprocesses provide an alternative to traditional extraction and chemical production methods. However, a significant limitation is that current bioprocess technology is often not economically competitive with more traditional production methods. The relatively high cost of production using bioprocess technology comes from a number of sources, including high maintenance costs of bioreactor equipment, expensive reagents for inducing microbial production and cell growth, and low product production due to the toxic effects of bioproduction on the microbial cell culture. This toxicity, or biosynthetic burden, places significant limits on the maximum level of product synthesis and hinders the rate at which product-synthesizing bacterial cells can produce product and divide.

One common obstacle in achieving high biosynthetic product yield from bioprocesses is the rapid accumulation in such microbial cultures of genetic mutants where product synthesis is reduced or non-existent. Such mutants have a selective advantage over producing cells due to a lower metabolic burden or lower product toxicity experienced by the mutant when compared to the producing cells. As a consequence, a large fraction of the microbial culture can be overtaken by non-producing mutant cells, thus reducing overall product yield. Conventional methods utilized to restore product yield include renewing the microbial culture. However, culture renewal is time consuming, inefficient and increases technological complexity of the bioprocess.

Microbial cells used for some bioprocesses require special induction conditions, such as temperature or culture density, or specific chemical signals, such as small molecule inducing agents, in order to begin producing product. Using these techniques to achieve culture induction in large-scale bioprocess facilities can add significant expense.

Bioprocesses suffer another drawback when utilized to produce complex molecules. Complex molecules typically require a multi-step synthesis process in which multiple bacterial cultures are mixed to produce different intermediates of the molecule synthesis pathway. However, mixed cultures are very difficult to control and utilizing separate bioreactors for individual bacterial cultures is costly and inefficient.

Accordingly, what is needed in the art are improved methods and materials for controlling microbial cell cultures.

SUMMARY

In one embodiment, a method of establishing microbial cell types is provided. The method includes modifying microbial cells with a genetic circuit, the genetic circuit configured to produce a localization factor exhibiting an asymmetric localization pattern as a basis for asymmetric cell division, the asymmetric cell division facilitating establishment of distinct cell types within a population of microbial cells. The genetic circuit is also configured to produce a signaling factor linked to the localization factor to form a biochemical platform, the biochemical platform eliciting differentiable cell behavior in microbial cells that inherit the biochemical platform.

In another embodiment, a chemically inducible genetic for tuning a population distribution of microbial cells is provided. The chemically inducible genetic circuit includes a protein factor exhibiting subcellular polar localization for directing an establishment of distinct cell types within the population of microbial cells, an enzyme fused to the protein factor to form a complex, the enzyme establishing a gradient of a small molecule that elicits a programmable pattern of gene expression, and a chemically inducible promoter located upstream of genetic coding sequences of the complex.

In yet another embodiment, an optogenetic circuit for tuning a population distribution of microbial cells is provided. The optogenetic circuit includes a photo-controllable transcriptional regulation system, a localization factor exhibiting subcellular polar localization for directing an establishment of distinct cell types within a population of microbial cells, a signaling factor linked to the localization factor to form a biochemical platform, the signaling factor catalyzing production of a secondary messenger molecule that is asymmetrically distributed during cell division, the asymmetric distribution of the secondary messenger molecule facilitating a differential program of gene expression in two or more daughter cells, and a promoter linking the photo-programmable transcription regulation system to production of the localization factor and the signaling factor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 5A illustrates a physical map of a plasmid listed in Table 1 according to an embodiment described herein.

FIG. 5B illustrates a physical map of a plasmid listed in Table 1 according to an embodiment described herein.

FIG. 5C illustrates a physical map of a plasmid listed in Table 1 according to an embodiment described herein.

FIG. 5D illustrates a physical map of a plasmid listed in Table 1 according to an embodiment described herein.

FIG. 5E illustrates a physical map of a plasmid listed in Table 1 according to an embodiment described herein.

FIG. 5F illustrates a physical map of a plasmid listed in Table 1 according to an embodiment described herein.

FIG. 5K illustrates a physical map of a plasmid listed in Table 1 according to an embodiment described herein.

FIG. 5L illustrates a physical map of a plasmid listed in Table 1 according to an embodiment described herein.

FIG. 5M illustrates a physical map of a plasmid listed in Table 1 according to an embodiment described herein.

FIG. 5N illustrates a physical map of a plasmid listed in Table 1 according to an embodiment described herein.

FIG. 5O illustrates a physical map of a plasmid listed in Table 1 according to an embodiment described herein.

Figure 1A:
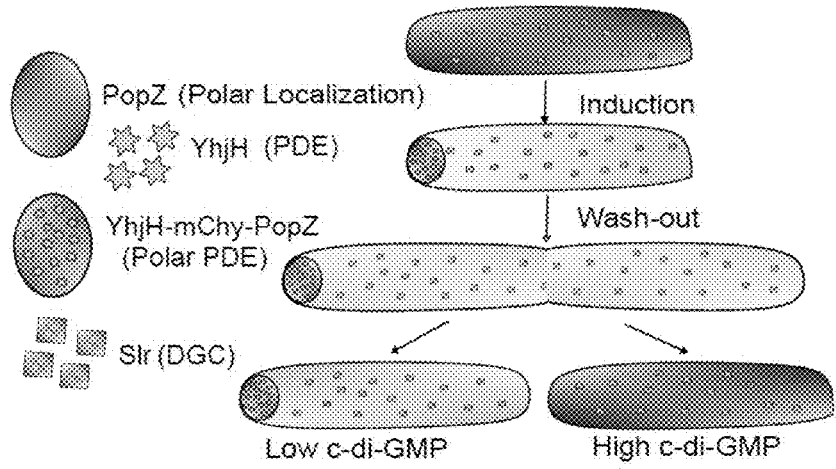
FIG. 1A illustrates a conceptual diagram of a method for utilizing asymmetric cell division to generate distinct cell types according to an embodiment described herein.

Figures included herein illustrate various embodiments of the disclosure. It is contemplated that elements and features of one embodiment may be beneficially incorporated in other embodiments without further recitation.

DETAILED DESCRIPTION

The present disclosure relates to microbial stem cell technology that enables a growing microbial culture to stably maintain two or more distinct cell types in a ratio that can be genetically programmed and/or dynamically controlled during cultivation. It is contemplated that embodiments described herein can be utilized to increase product yield in microbial fermentations and advanced engineering of biomaterials using genetically engineered microbial cells, among others.

Asymmetric bacterial cell division produces daughter cells with different identities and patterns of gene expression. Polarized distributions of regulatory proteins and the associated asymmetry in signaling networks within bacterial cells often influence such division and gene expression. Cellular division and gene expression are fundamental to multicellular development and the benefits that are derived from collaborating cell types.

In one embodiment, a method for inducing a program of asymmetric cell division coupled with cell differentiation in microbial cells is provided. The method includes modifying microbial cells by placing in them a genetic circuit that is configured to produce an asymmetrically localized biomolecular platform. This biomolecular platform, in addition to having the property of asymmetric localization in pre-divisional cells, also has the function of driving a definable pattern of cell differentiation during cell division. A consequence is the establishment of multiple distinct, differentially controllable cell types within the population of microbial cells.

In one embodiment, a chemically inducible biochemical platform for establishing programmable asymmetric cell division in microbial cells is provided. The biochemical platform includes a protein that localizes to a discrete location or set of defined locations in the cell, and subsequently becomes asymmetrically distributed between daughter cells in the process of cell division. Asymmetric localization of this biochemical platform, including but not limited to the vicinity of the cell poles, serves as the basis for directing differentiation between daughter cells during cell division. In addition to having a localization activity, the biochemical platform also includes a directly or indirectly linked signaling factor which establishes a biologically differentiable trait that distinguishes those daughter cells that inherit the platform from siblings that do not.

In one embodiment, an optogenetic circuit for tuning a population distribution of microbial cells based on the expression or activity of the biochemical platform described above is provided. The optogenetic circuit includes a light-controllable transcriptional regulation system, which controls the expression or activity of said biochemical platform.

In one embodiment described herein, cell geometry and transcriptional control elements from multiple bacterial species are combined to create a unique and robust synthetic genetic circuit for establishing programmable asymmetric cell division in commercially significant bacterial species such as *E. coli*. For example, individual components include the polar organizing protein PopZ from Alphaproteobacteria and regulators of c-di-GMP dependent transcriptional activity from *Klebsiella* and other organisms.

According to embodiments described herein, seemingly complex biological phenomenon—asymmetric cell division and the generation of differentiated cell types—can be brought about by a small set of genes in a prokaryotic organism. The transcriptional output of the genetic circuit is directed to establish different sub-populations of differentiated cells. For example, the transcriptional output of the genetic circuit may establish motile versus non-motile cells or biosynthetically productive cells versus non-productive cells. In the productive cell versus non-productive cell implementation, productive "factory" cells express a set of enzymes in a biosynthetic pathway, while non-productive cells function as a regenerative population of stem cells, which produce a factory and a non-factory cell with every cell division. Thus, a first sub-population of differentiated cells established by methods herein may function to produce a biosynthetic product while a second sub-population functions to maintain the two or more sub-populations. Differentiable cell behavior traits may also include, for example, distinct programs of gene expression or differences in protein complex assembly.

In one embodiment described herein, population distribution of multiple cell types can be tuned using a chemically-regulated system that regulates expression of the localization factor by exposure to one or more chemicals. For example, population distribution of cell types may be tuned using a chemical inducer and a chemically-inducible promoter located upstream of genetic coding sequences of the localization factor. Alternatively, population distribution of cell types may be tuned using a chemical repressor.

Embodiments described herein also provide for population distribution of cell types which can be tuned using a light-activated system that regulates expression of the localization factor by exposure to certain wavelengths of light. In one embodiment, population distribution of cell types can be tuned using a light-activated system that regulates expression of the localization factor by exposure to light having a wavelength in the visible, infrared (IR), and/or ultraviolet (UV) portions of the electromagnetic spectrum. For example, population distribution of cell types can be tuned by exposure to red or green light. In some embodiments, the light-activated system regulates expression of the localization factor by controlling the activity of one or more signal transduction proteins. In one embodiment, the light-activated system regulates expression of the localization factor by controlling the activity of a histidine kinase.

The synthetic genetic circuits described herein provide a genetically programmable platform for leveraging asymmetric cell division of a genetically uniform population of microbial cells to create new types of collaborative microbial communities. More specifically, microbial stem cell technology enables maintenance of "stem" cells which are not burdened with biosynthetic product synthesis. Upon cell division, a "stem" cell produces daughter "factory" cells that are genetically programmed for product synthesis. The lack of selective pressure maintains "stem" cells free of mutations and capable of continually generating product synthesizing "factory" cells. In one embodiment, a ratio of "stem" to "factory" cells is genetically programmed and/or controlled by physiochemical stimuli, such as exposure to chemicals, light, and/or changes in temperature.

In order to produce different cell types, such as "stem" and "factory" cell types, a localization factor that accumulates at an asymmetric location in a pre-divisional cell is utilized. In one embodiment, the localization factor is a protein factor. The localization factor may be any suitable protein that self-assembles into a large complex or macromolecular structure, and/or accumulates in a certain subcellular locations. In one example, the localization factor accumulates at one or both cell poles in various rod-shaped bacteria. In one embodiment, the localization factor is a polar organizing protein PopZ, or a homolog thereof. PopZ is a conserved protein from the class Alphaproteobacteria. In *E. coli*, a common host of bacterial fermentations, PopZ compactly accumulates at a single cell pole. When such a cell divides, the cell produces one daughter cell with PopZ (the "stem" or "progenitor" cell) and another daughter cell without PopZ (the "factory" cell), illustrated in the conceptual diagram of FIG. 1A.

In the absence of the polar PopZ, the "factory" cell continues to divide and give rise to new "factory" cells while the "stem" cell retains PopZ over several hours. With every cell division of the "stem" cell, the "stem" cell will continue to produce one new "factory" cell. In one embodiment, PopZ is fused to a signaling factor that establishes a gradient of a small molecule that facilitates the asymmetric distribution of PopZ protein in a programmable pattern of gene expression. The signaling factor may positively or negatively affect the gene expression of the small molecule. For example, the signaling factor may be an enzyme that catalyzes the production of a small molecule. The signaling factor may further be directly or indirectly linked to the PopZ protein. In one embodiment, the small molecule is a secondary messenger molecule. In one embodiment, the small molecule is a cyclic nucleotide-based second messenger. For example, the small molecule is cyclic-diguanosine monophosphate (c-di-GMP), cyclic-adenosine-monophosphate (cAMP), cyclic-di-adenosine monophosphate (c-di-AMP), cyclic guanosine monophosphate (cGMP), and c-di-AMP/GMP.

The PopZ protein may be fused to any suitable signaling factor to form a PopZ-signaling factor complex establishing a gradient of the small molecule regulating gene expression. For example, the PopZ protein may be fused to an enzyme, such as a kinase, phosphatase, protease, protease adaptor protein, or the like. In one embodiment, PopZ is fused to an enzyme that produces c-di-GMP or a precursor thereof. In one embodiment, PopZ is fused to an enzyme that specifically degrades c-di-GMP. For example, PopZ is fused to a phosphodiesterase. Thus, cells that retain PopZ at a single pole also maintain a low level of intracellular c-di-GMP, whereas "factory" cells have higher levels of naturally synthesized intracellular c-di-GMP.

A genetic element may be further utilized to induce the expression of enzymes that catalyze synthesis a desired biosynthetic product. In one embodiment, the enzyme is diguanylate cyclase and synthesizes c-di-GMP from the intracellular pool of guanosine triphosphate (GTP). In one embodiment, the genetic element includes a c-di-GMP-sensitive transcription factor MrkH and a PmrkA promoter regulated by MrkH. It is believed that the genetic element can be utilized to differentially control gene expression of a desired biosynthetic product. For example, PmrkA is utilized to drive expression of a gene encoding a desired fermentation product(s). As c-di-GMP accumulates in "factory" (but not "stem") cells, the c-di-GMP binds to MrkH, which in turn binds to the PmrkA promoter and activates target gene expression. Thus, asymmetric cell division may be used to induce production in cells that lacking the localization factor.

In one embodiment, genetic engineering utilizes a factor, such as the localization factor described above, that exhibits properties of subcellular localization as the basis for directing the establishment of distinct cell types in a population of microbial cells.

In another embodiment, the factor is utilized as the basis for controlling gene expression of a multi-gene biosynthetic product pathway.

In another embodiment, a group of genetic cassettes that utilize the factor that has the property of subcellular localization are utilized as the basis for directing the establishment of distinct cell types in a population of microbial cells.

In another embodiment, a group of genetic cassettes carry the sequences encoding the PopZ-signaling factor complex utilized as the basis for directing the establishment of distinct cell types in a population of microbial cells.

In another embodiment, the PopZ-signaling factor complex is further fused to a third protein to form a tripartite protein complex utilized as the basis for directing the establishment of distinct cell types in a population of microbial cells.

In one embodiment, the signaling factor is a member of a split protein system, and is utilized as the basis for conditional reconstitution of protein activity.

In another embodiment, *Caulobacter crescentus* PopZ, a homolog of PopZ, or a variant or fragment thereof, is utilized as the basis for directing the establishment of distinct cell types in a population of microbial cells.

In another embodiment, a bacterial polar organizing protein, or a variant or fragment thereof, is utilized as the basis for directing the establishment of distinct cell types in a population of microbial cells.

In another embodiment, a polar landmark or hub protein, such as HubP from the gammaproteobacteria class of bacteria, is utilized as the basis for directing the establishment of distinct cell types in a population of microbial cells.

In another embodiment, an outer membrane autotransporter protein, such as IcsA, is utilized as the basis for directing the establishment of distinct cell types in a population of microbial cells.

In another embodiment, multiple cell types with distinct patterns of gene expression from a genetically uniform population of microbial cells are established and controlled by the use of a factor that has the following properties: subcellular localization, and the ability to control gene expression, either through direct manipulation of transcriptional machinery or indirectly through control of factors that regulate transcriptional activity.

In another embodiment, different patterns of gene expression among distinct cell types in a population of microbial cells are controlled through a mechanism that regulates the levels of a secondary messenger, such as a small molecule signal.

In another embodiment, different patterns of gene expression among distinct cell types in a population of microbial cells are controlled through a mechanism that uses a factor that has subcellular localization characteristics as the basis for controlling differential gene expression.

In another embodiment, protein-protein interactions in a population of microbial cells can be controlled through a mechanism that uses a factor that has subcellular localization characteristics. For example, the mechanism may be utilized to conditionally reconstitute a split protein system, such as green fluorescent protein (GFP).

In one embodiment, the signaling factor is a member of a split protein system.

In another embodiment, the system is not limited to *E. coli* but may work in many other cell types (prokaryotic and eukaryotic).

In another embodiment, the system components (geometric organizer, secondary messengers, transcription control, etc.) can originate from any organism. In one embodiment, components from *Caulobacter, Klebsiella, Synechocystis, Rhodobacter, Xanthomonas*, and plasmids of various types are utilized.

In another embodiment, various second messengers (in addition to c-diGMP) can be used to establish control of gene regulation, both nucleotide messengers and nonnucleotide. For example, cyclic adenosine monophosphate (cAMP) or calcium ions may be utilized to establish control.

In another embodiment, the output of the system does not have to be transcriptional activity, but could be other types of activity, such as motor protein activity, enzymatic activity or protein interaction.

In one embodiment, the genetic circuit is used to separate a multi-step biosynthetic pathway into multiple stages, each stage being activated in a distinct differentiated cell type within a community of microbial cells. For example, distinct components or precursor of a desired biosynthetic product may be produced in distinct cell types.

In another embodiment, the localization factor may be non-localized to the cell pole, and it may be non-homologous to PopZ.

In another embodiment, multiple PopZ or other geometric organizing proteins can be applied to diversify the activities that are being controlled.

In another embodiment, various stimuli can control the system, including a broad range of electromagnetic wavelengths, chemical, thermal, or mechanical stimuli. For example, small molecules and visible light are suitable for utilization as independently usable stimuli.

Experimental Methods and Materials

Formation of Different Cell Types Based on Differential Accumulation of Small Molecules Table 1 below provides a summary of plasmids utilized in the experimental methods and procedures described herein. It is contemplated that any suitable vector may be utilized to carry out the methods described herein.

TABLE 1

| Plasmid name | Essential genes and regulatory elements | Antibiotic resistance |
|---|---|---|
| pBAD | araBADp promoter (SEQ ID No. 2); MCS | Amp |
| pACYC | T7p promoter (SEQ ID No. 22); MCS | Cam |
| pBAD-YmP | yhjH-mCherry-popZ fusion protein (under araBADp promoter) (SEQ ID No. 28) | Amp |
| pBAD-YmP-B | yhjH-mCherry-popZ (under araBADp promoter); bphS-bphO (under tetp promoter) (SEQ ID Nos. 3-4) | Amp |
| pBAD-YmP-S | yhjH-mCherry-popZ (under araBADp promoter); slr1143 (under tetp promoter) (SEQ ID No. 20) | Amp |
| pAC-YmP-B | yhjH-mCherry-popZ (under T7p promoter); bphS-bphO (under tetp promoter) | Cam |
| pAC-YmP-S | yhjH-mCherry-popZ (under T7p promoter); slr1143 (under tetp promoter) | Cam |
| pMQ-132 split GFP | pilZ-gfp10 (SEQ ID No. 11); fimX-gfp11 (under lacp promoter) (SEQ ID No. 9); gfp1-9 (under T7p promoter) (SEQ ID No. 10) | Gent |
| pMAL-Slr1143 | slr1143 (under tacp promoter) | Amp |
| pMAL-p2x | tacp promoter; MCS | Amp |
| pBAD-MrkH | c-di-GMP dependent transcription factor mrkH (SEQ ID No. 15) under araBADp promoter | Amp |
| pB-Mrk-GFP | mrkH (under araBADp promoter); monomeric superfolder msf-gfp (under mrkAp promoter) (SEQ ID No. 16) | Amp |
| pB-Mrk-rbsGFP | mrkH (under araBADp-promoter); msf-gfp (under mrkAp promoter with strong RBS) | Amp |
| pCDF-pMrkA-GFP(-) | mrkAp-gfp with restriction sites downstream msf-gfp for insertion of additional components | Spec |
| pBAD-M-G-W | mrkH (under araBADp-promoter); gfp, ac-CoA reductase & WE synthase as a poly-cistronic message under mrkAp promoter | Amp |
| pSR58-6 (pCR) | ccaR response regulator (SEQ ID No. 6); PcpcG2-172 promoter, controlling expression of GFP | Cam |
| pCRP | ccaR response regulator; ccaRp promoter (SEQ ID No. 7), yhjH-mCherry-popZ | Cam |

TABLE 1-continued

| Plasmid name | Essential genes and regulatory elements | Antibiotic resistance |
|---|---|---|
| pNO286-3 (pCS) | ccaS light inducible histidine kinase (SEQ ID No. 8); ho1 & pcyA genes (SEQ ID Nos. 12, 17), responsible for PCB chromophore biosynthesis | Spec |
| pCRPMG | ccaR response regulator; ccaRp promoter; yhjH-mCherry-popZ; mrkH (under araBADp promoter); mrkAp promoter; msf-gfp reporter | Cam |
| pCSTS | ccaS light inducible histidine kinase; ho1 & pcyA genes, responsible for PCB chromophore biosynthesis; slr1143 (under tetp promoter control) | Spec |
| pCRPMG-Mot | ccaR response regulator; ccaRp promoter; yhjH-mCherry-popZ; mrkH (under araBADp promoter); mrkAp promoter, controlling expression of msfGFP and motA, motB genes | Cam |

FIG. 1A illustrates a conceptual diagram of a method for using polar asymmetry to generate two distinct cell types. "Induction" refers to the production of the biochemical platform, herein labeled "YhjH-mChy-PopZ," having the localization factor PopZ. "Wash-out" refers to a stoppage in biochemical platform production. Asymmetric cell division occurs subsequent to "wash-out". "High c-di-GMP" and "low c-di-GMP", together with the "YhjH" and "Slr" signaling components of the genetic circuit, provide an example of a system that gives rise to differentiable cell types based on differentiable cell behavior.

To facilitate phenotypic differences between "stem" cells and "factory" cells, the PopZ protein was linked to the c-di-GMP signaling system by fusing PopZ (SEQ ID No. 18) with a c-di-GMP phosphodiesterase YhjH (SEQ ID No. 25) from $E.$ $coli$ and a red fluorescent protein mCherry (mChy) (SEQ ID No. 13). YhjH and mChy were translationally fused with the N-terminus of PopZ using 9- and 12-amino acid linker sequences to form the tripartite YhJh-mChy-PopZ biochemical control platform.

Figure 1B:
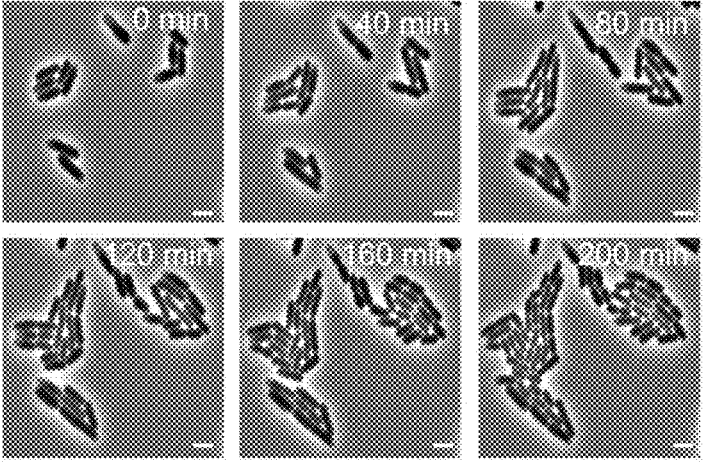
FIG. 1B illustrates images of two cell types with a fluorescent signal overlaid on the image according to an embodiment described herein.
Figure 1C:
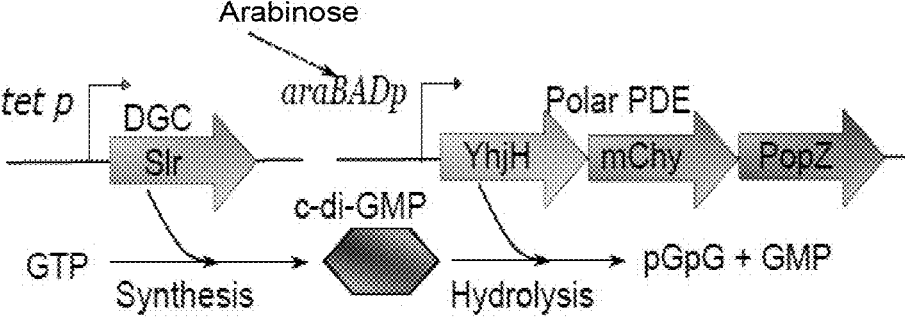
FIG. 1C illustrates a schematic diagram of a genetic circuit for controlling c-di-GMP levels in asymmetrically dividing cells according to an embodiment described herein.

FIG. 1B includes time lapse fluorescence microphotographs depicting the asymmetric cell division generating of two distinct cell types characterized by the presence of the YhjH-mChy-PopZ biochemical platform (exhibiting red fluorescence) over a 200 minute time course. To confirm whether YhjH-mChy-PopZ forms polar complexes that asymmetrically distribute between dividing cells, the YhjH-mChy-PopZ biochemical platform was expressed in $E.$ $coli$ cells of the strain MG-1655 DE3. The cells were transformed with the plasmid pBad-YmP (plasmid map shown in FIG. 5A) having YhjH-mChy-PopZ fused downstream of an araBAD promoter via isothermal Gibson Assembly, thus having expression of the YhjH-mChy-PopZ biochemical platform regulated by arabinose. FIG. 1C illustrates the genetic circuit comprising the YhJh-mChy-PopZ biochemical platform, wherein YhjH catalyzes the hydrolysis of c-di-GMP into pGpG, a linear diguanylate and hydrolysis product of c-di-GMP, and guanosine monophosphate (GMP).

The MG-1655 DE3 cells were grown at 37° C. overnight in lysogeny broth (LB) media with the addition of appropriate antibiotics. The cells were then diluted 100 times and grown on a rotary drum in 2 ml volumes in glass tubes for 2 hours prior to protein expression activation. Expression of the YhjH-mChy-PopZ biochemical platform was induced for two hours using 0.2% of L-arabinose, followed by wash-out and removal of the L-arabinose. The L-arabinose inducer was removed by three repeats of pelleting the cells with micro-centrifugation at 9000 rpm and re-suspending the cells in fresh LB media. Prior to the subsequent chase period in which cells were inoculated without the inducer, the cells were diluted 5 times and incubated at 37° C. in 150 ml flasks with shaking at 250 rpm. The growing cultures of cells were continuously diluted by removing portions of media containing cells and adding fresh LB media to keep the cell cultures in a log growth phase, with an optical density (OD 600) in a range between 0.3 to 0.6.

To obtain the live-cell images in FIG. 1B, cells were immobilized on 1% agarose pads and imaged with a Zeiss Axio Imager Z2 epifluorescence microscope equipped with a Hamamatsu Orca-Flash4 sCMOS camera and a Plan-Apochromat 100×/1.46 Oil Ph3 objective. A Zeiss filter set 63HE was utilized to acquire the fluorescent signal of mChy and the images were collected and processed with Zen Blue software. It was observed that after transient expression of YhjH-mChy-PopZ, the next cell division was asymmetric with respect to the inheritance of PopZ and the accumulation of c-di-GMP levels.

Figure 1D:
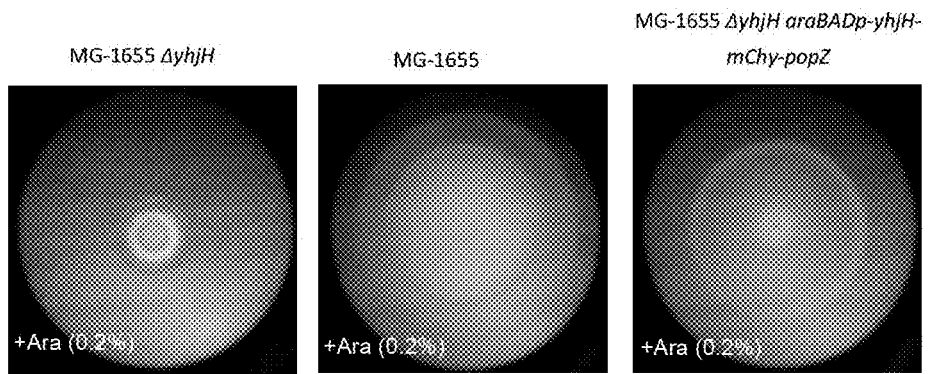
FIG. 1D illustrates images of cell motility in agar of three cell types according to an embodiment described herein.

To confirm whether the tripartite YhjH-mChy-PopZ biochemical platform retained phosphodiesterase activity upon transformation, YhJh-mChy-PopZ was expressed in an $E.$ $coli$ mutant strain MG1566 ΔyhjH with impaired motility in the presence of high c-di-GMP levels and compared to the wild-type MG1655 strain, which is characterized as being constitutively motile. The motility phenotype associated with the mutant MG1566 ΔyhjH strain in semi-solid agar was rescued by transforming the mutant cells with the plasmid pBad-YmP (plasmid map shown in FIG. 5A) and inducing expression of the tripartite YhJh-mChy-PopZ biochemical platform, thus suggesting that phosphodiesterase activity was retained. FIG. 1D illustrates swarm motility results of the mutant strain MG1566 ΔyhjH (left), the wild-type strain MG1655 (center), and the transformed mutant strain (right). To test the motility phenotype, 3 μl of log-phase cells were spotted on semi-solid agar plates comprising 1% tryptone, 0.5% sodium chloride, and 0.25% agar. The cells were grown for 7 hours at 37° C. in presence of 0.2% L-arabinose.

The difference in intracellular c-di-GMP levels between "factory" cells and "stem" cells was further enhanced by introduction of a c-di-GMP synthesizing enzyme diguanylate cyclase (DGC), depicted in the genetic circuit diagram in FIG. 1C. It is contemplated that modest DGC activity can raise c-di-GMP levels in "factory" cells while not overcoming the c-di-GMP hydrolytic activity of the YhjH-mChy-PopZ biochemical platform in "stem" cells. To determine the influence of DGC on the asymmetrically dividing cell lines, MG-1655 DE3 cells capable of gene expression using a T7 promoter expression platform were transformed with the plasmid pAC-YmP-B or pAC-YmP-S (plasmid maps shown in FIG. 5B-5E).

Figure 1E:
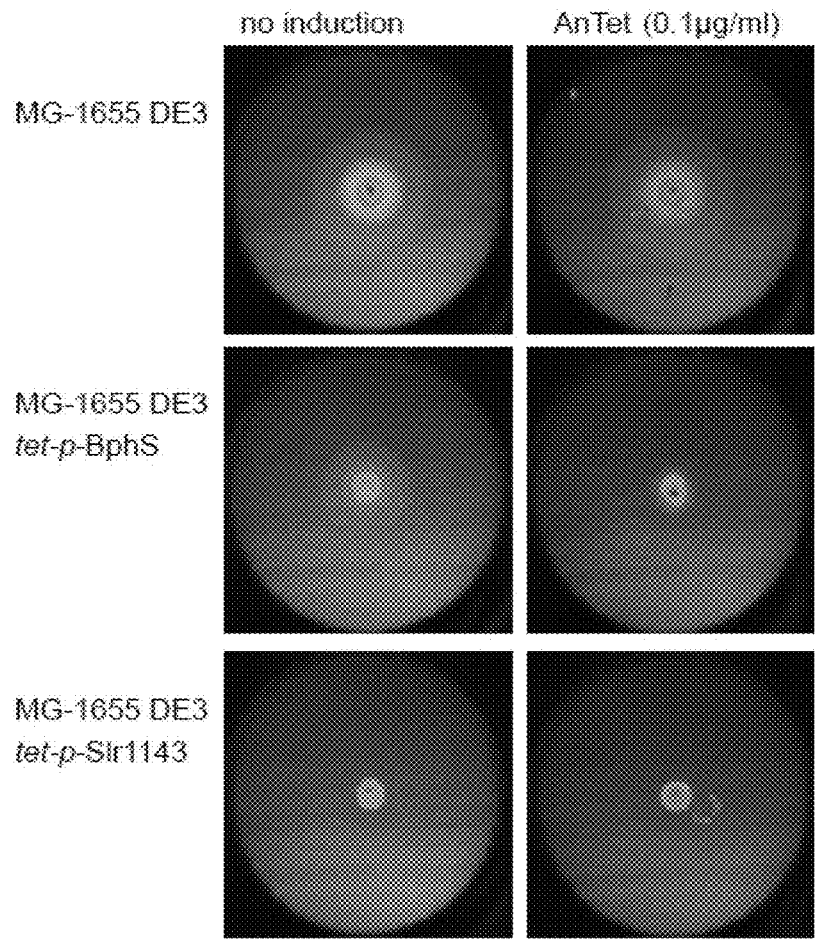
FIG. 1E illustrates images of cell motility in agar of three cell types according to an embodiment described herein.

FIG. 1E illustrates the motility of these cells under conditions of DGC induction or no induction. The plasmid pAC-YmP-B (middle panels) included a less active DGC, BphS, while the plasmid pAC-YmP-S (lower panels) included a stronger DGC, Slr1143. The right panels of FIG. S1B depict cells under strong DGC induction in the presence of 0.1 μg/ml anhydrotetracylcine, while the left panels depict basal DGC expression from the leaky tetp promoter. The cells transformed with pAC-YmP-S exhibited inhibited motility under both strong DGC induction and basal DGC expression, whereas cells transformed with pAC-YmP-B were induced with anhydrotetracycline to achieve inhibited motility. The control host strain, not bearing any plasmids, retained the motile state (FIG. 1E upper panel).

Figure 2A:
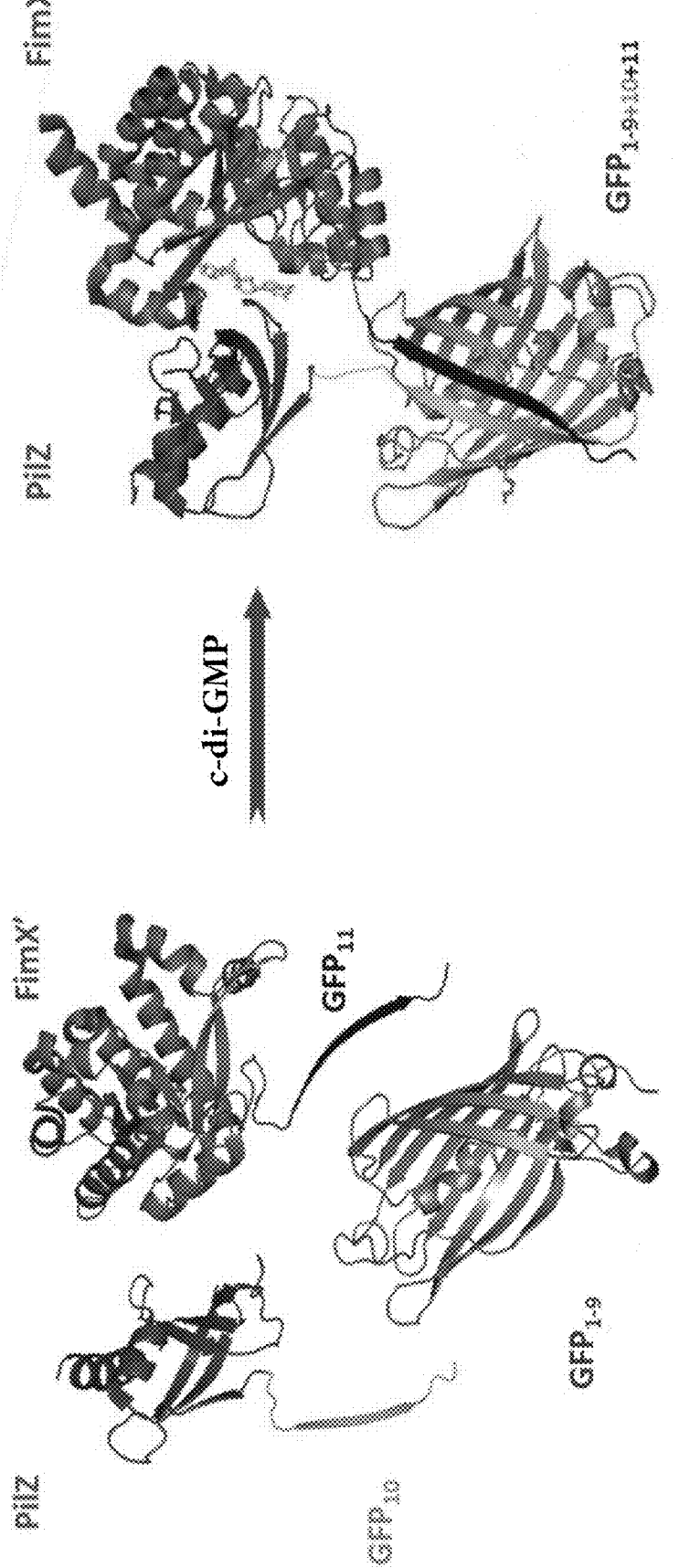
FIG. 2A illustrates a conceptual diagram of a tripartite split-GFP reporter system according to an embodiment described herein.

Next, the C-di-GMP levels in "factory" and "stem" cells were monitored using a fluorescent tripartite split-protein c-di-GMP reporter system having the $Xanthomonas$ $campestris$ proteins FimX and PilZ translationally fused to a green fluorescent protein (GFP) beta-barrel, as illustrated in FIG. 2A. FimX and PilZ were selected due to their enhanced interaction in the presence of c-di-GMP. Beta-strand 11 ($GFP_{11}$) of GFP was fused to the C-terminus of the c-di-GMP binding EAL domain of FimX and beta-strand 10 ($GFP_{10}$) of GFP was fused to the N-terminus of PilZ, respectively, using 10-amino acid long flexible GS-linkers. The remaining non-fluorescent portion of the GFP beta-barrel comprising beta-strands 1-9 ($GFP_{1-9}$) was expressed separately.

Figure 2B:
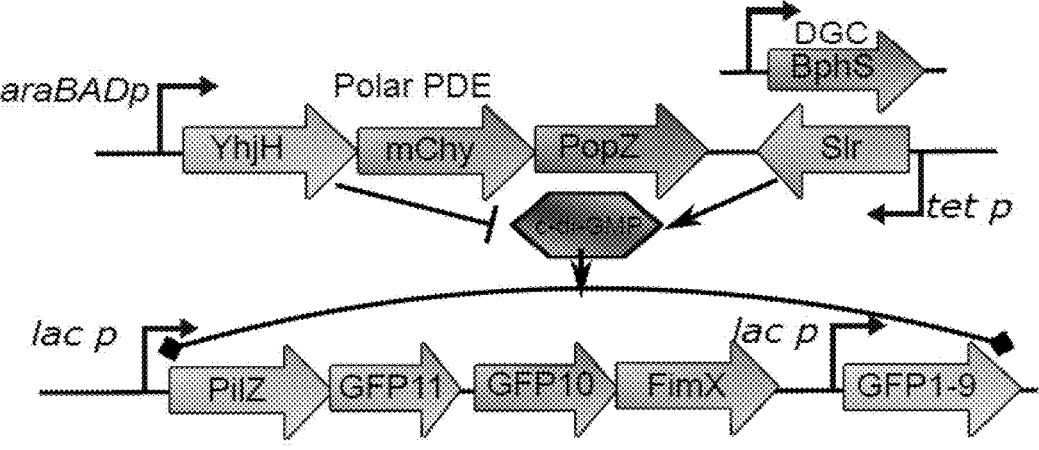
FIG. 2B illustrates a schematic diagram of a genetic circuit for detecting c-di-GMP levels in asymmetrically dividing cells according to an embodiment described herein.

To clone the DNA constructs of the split-GFP c-di-GMP reporter system, nucleotide sequences encoding FimX ($XccFimX^{EAL}$), PilZ ($XccPilZ_{1028}$), and split GFP fragments ($GFP_{10}$, $GFP_{11}$, and $GFP_{1-9}$) were codon-optimized and synthesized as two DNA strings. The final construct (SEQ ID No. 32) was assembled via Gibson assembly procedure, on a pMQ132 plasmid (plasmid map shown in FIG. 5F). FIG. 2B illustrates genetic circuits comprising the split-protein c-di-GMP reporter system.

Figure 2C:
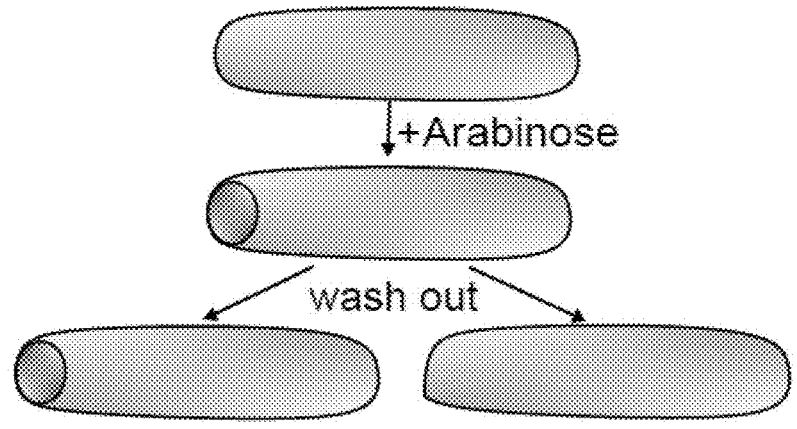
FIG. 2C illustrates a conceptual diagram of a method for utilizing the split-protein c-di-GMP reporter system to detect c-di-GMP levels in asymmetrically dividing cells according to an embodiment described herein.

It is contemplated that the FimX domain binds to the PilZ domain in the presence of c-di-GMP, thus bringing $GFP_{10}$ and $GFP_{11}$ together. The close proximity of $GFP_{10}$ and $GFP_{11}$ causes the spontaneous formation of an antiparallel beta sheet complementing $GFP_{1-9}$, resulting in GFP fluorescence. FIG. 2C illustrates a conceptual diagram of a method for using the split-protein c-di-GMP reporter system in combination with the YhjH-mChy-PopZ biochemical platform to monitor both "factory" cells and "stem" cells via characteristic c-di-GMP levels.

Figure 2D:
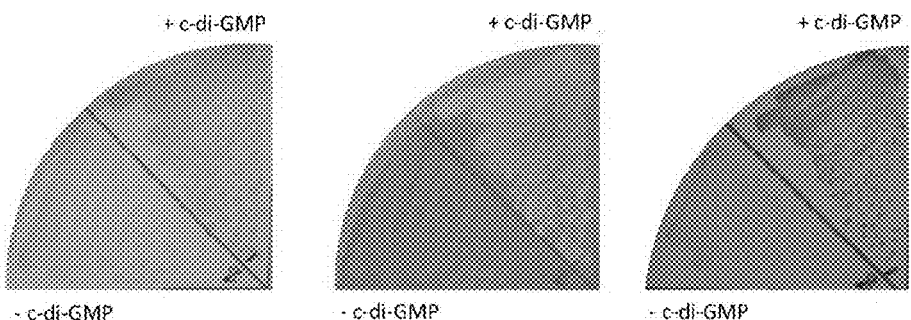
FIG. 2D illustrates images of two cell types cultured on plated media at an indicated time according to an embodiment described herein.

To characterize the interactions of Fim X and PilZ, fluorescence was compared between cells of the $E.$ $coli$ strain BL21 (DE3) expressing components of the split-GFP system and transformed with either the plasmid pMAL-Slr1143 having the highly active DGC Slr1143 or empty plasmid, as illustrated in FIG. 2D. Individual bacterial colonies were streaked on LB media plates supplemented with appropriate antibiotics and 10 μM isopropyl β-D-1-thiogalactopyranoside (IPTG) at 37° C. for 24 hours. FIG. 2D illustrates the same plate under white light (left panel) and ultraviolet light, which excites GFP fluorescence (center panel). The relative levels of c-di-GMP levels in the cells were observed indirectly by Congo Red staining, which labels the curly fimbriae that are produced by $E.$ $coli$ in response to c-di-GMP (right panel). The split-GFP c-di-GMP reporter system produced fluorescence in high c-di-GMP cells expressing DGC Slr1143 (top sectors) and exhibited little or no fluorescence in low c-di-GMP cells lacking DGC Slr1143 (bottom sectors).

The split-GFP c-di-GMP reporter system was further tested using two genetic circuits differing in the level of DGC activity, also depicted in FIG. 2B (top right). Cells of the strain MG-1655 DE3 were transformed with either the pBAD-YmP-B or pBAD-YmP-S plasmid (plasmid maps shown in FIGS. 5B-5E) containing components for controlling c-di-GMP levels (YhjH-mChy-PopZ biochemical platform and a DGC) and the pMQ132-splitFRP plasmid (plasmid map shown in FIG. 5F) containing components for detecting c-di-GMP (split-protein c-di-GMP reporter system). Cells transformed with the pBAD-YmP-B plasmid expressed the less active DGC, BphS, while cells transformed with the pBAD-YmP-S plasmid expressed the more active DGC, Slr1143.

Figure 2E:
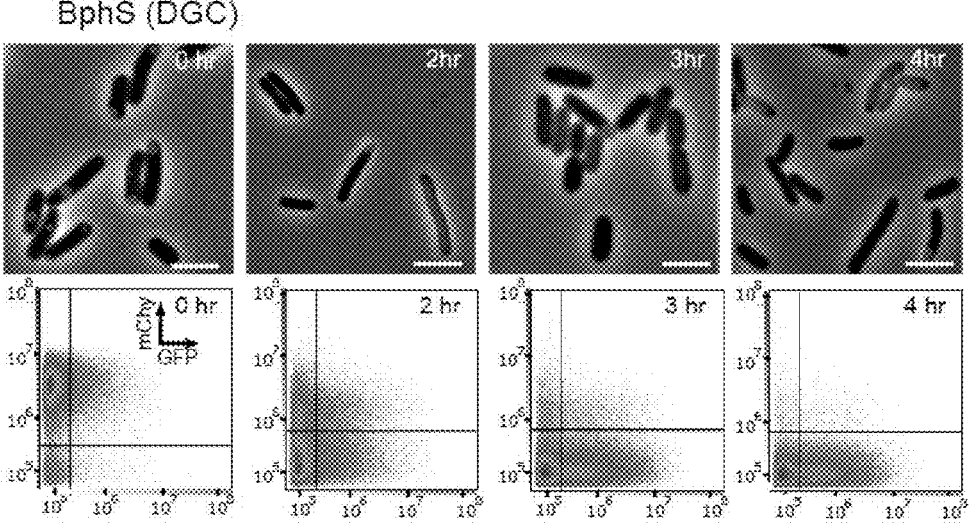
FIG. 2E illustrates images of cells at indicated times during cellular division and corresponding flow cytometry analysis of the cell populations according to an embodiment described herein.
Figure 2F:
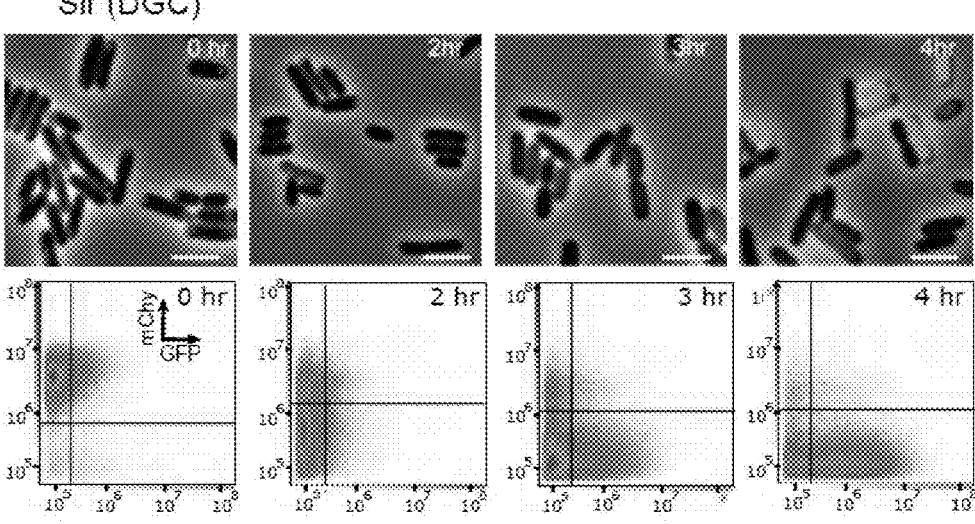
FIG. 2F illustrates images of cells at indicated times during cellular division and corresponding flow cytometry analysis of the cell populations according to an embodiment described herein.

FIGS. 2E and 2F depict fluorescence microphotographs (top panels) and flow cytometry data (lower panels) of the cells over a 4 hour time course. After a two-hour induction period with 0.2% L-arabinose, 80-90% of the cells contained the YhJh-mChy-PopZ biochemical platform and exhibited little to no GFP fluorescence. After subsequent rounds of cell division in the absence of the inducer, the fraction of GFP-positive cells ("factory" cells) and the intensity of GFP signal increased while the fraction of cells containing YhjH-mChy-PopZ foci ("stem" cells) decreased. Furthermore, the percentage of double-positive cells was less than 1%. Thus, asymmetric division of the MG-1655 DE3 cells produced two cell types that can be differentiated on the basis of c-di-GMP levels.

Moreover, the cell types produced are functionally differentiable on the basis of the c-di-GMP dependent tripartite YhJh-mChy-PopZ. The flow cytometry data (lower panels) demonstrates that the main cell population experiences a transient dark phase, when they have neither YhjH-mChy-PopZ nor GFP expression. These cells may be low in c-di-GMP levels because they are only a few divisions away from the YhjH-mChy-PopZ containing ancestor, and have not yet accumulated sufficient c-di-GMP for assembly of the split-GFP c-di-GMP reporter system. Consistent with this interpretation, cells expressing the stronger of the two DGCs, Slr1143 (FIG. 2E), exhibited higher GFP levels and had a lower fraction of double negative cells compared to cells expressing BphS (FIG. 2F).

Fluorescence microphotographs were generated using the methods described above while also using a Zeiss Filter set 38HE to acquire GFP fluorescent signals and overlaying GFP and mChy signals on a phase contrast image (grayscale). For flow cytometry analysis, 200 μL samples of cells were fixed in 4% paraformaldehyde for 30 minutes, then washed and incubated in phosphate-buffered saline, before being stored at 4° C. From 100,000 to about 500,000 cells from each sample were analyzed by a Yeti Cell Analyzer flow cytometer (Propel Labs, Ft. Collins, Co.) utilizing Everest software. Cells were gated using linear forward scatter (FS) by log side scatter (SS), followed by gating on FS area by FS height for aggregate exclusion. Fluorescence data was collected using a 525/35 nm filter from the 488 nm laser line for GFP and a 615/20 nm filter from the 561 nm laser line for mChy. The data was analyzed using Kaluza Flow Cytometry Analysis Software (Beckman Coulter Life Sciences, Indianapolis, IN). For all flow cytometry data plots, fluorescence intensity of GFP is plotted on the X axis while mChy is plotted on the Y axis. The flow cytometry data plots in FIG. 2E show data from a single trial. All samples were collected, prepared, stored, and analyzed using the same methods.

Translating Differential Accumulation of Small Molecules into Differential Gene Expression To facilitate differential gene expression patterns between "stem" cells and "factory" cells having asymmetric c-di-GMP distribution, a c-di-GMP-dependent transcriptional factor and reporter system from *Klebsiella pneumoniae* was utilized instead of the split-GFP c-di-GMP reporter system. The transcriptional factor and reporter system includes a transcriptional activator MrkH, which binds to a cognate promoter mrkAp (SEQ ID No. 14) in the presence of c-di-GMP, illustrated in the genetic circuit diagram of FIG. 3A (bottom). Binding of MrkH with mrkAp therein activates expression of downstream genes, such as gfp. The components for c-di-GMP dependent expression of GFP were inserted into a pBAD plasmid vector, resulting in a pBAD-Mrk-GFP plasmid providing moderate levels of GFP expression or a pBAD-Mrk-rbs-GFP plasmid providing higher levels of GFP expression (plasmid maps shown in FIGS. 5H-5I). To make the MrkH-mrkAP transcriptional factor and reporter system (SEQ ID No. 29) compatible with the tripartite YhJh-mChy-PopZ biochemical control platform, YhJh-mChy-PopZ expression was transferred to a pACYC plasmid backbone having an IPTG-inducible T7 promoter expression platform such as pAC-Ymp-B or pACYC-YmP-S (top) (plasmid maps shown in FIGS. 5B-5E).

Figure 5G:
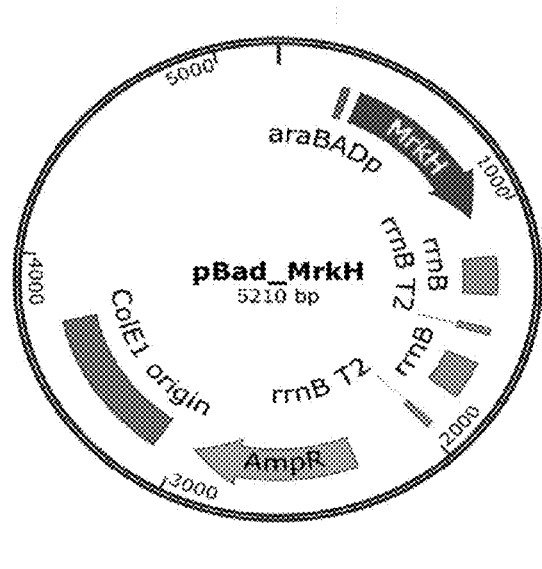
FIG. 5G illustrates a physical map of a plasmid listed in Table 1 according to an embodiment described herein.
Figure 5H:
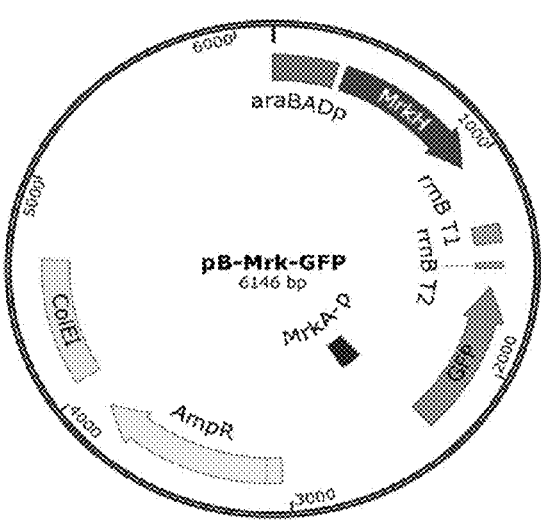
FIG. 5H illustrates a physical map of a plasmid listed in Table 1 according to an embodiment described herein.
Figure 5I:
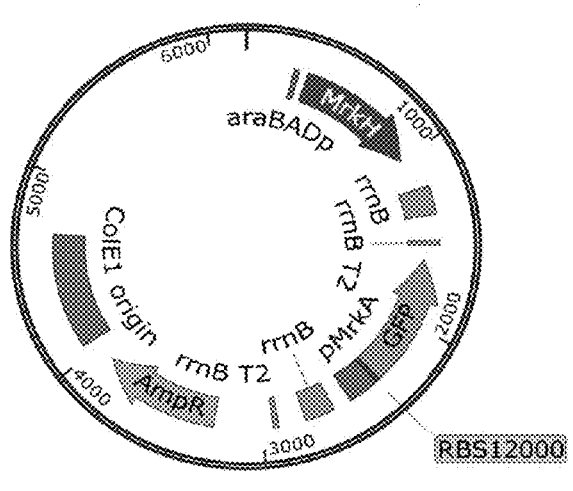
FIG. 5I illustrates a physical map of a plasmid listed in Table 1 according to an embodiment described herein.

To clone the MrkH-mrkAP transcriptional factor and reporter system into a pBAD plasmid, the coding sequence for MrkH, followed by a bi-directional terminator, was amplified from a template plasmid and cloned into the pBAD plasmid via isothermal Gibson assembly, resulting in a pBAD-MrkH plasmid (plasmid map shown in FIG. 5G). Subsequently, the mrkAp promoter sequence, and a GFP coding sequence were cloned downstream of the terminator and in the opposite transcriptional direction to mrkH, resulting in a pB-Mrk-GFP plasmid (plasmid map shown in FIG. 5H). As an alternative, MrkAp-gfp was modified by insertion of a stronger RBS upstream GFP. Isothermal assembly of mrkAp-rbs and gfp into the pBAD-MrkH plasmid vector produced the plasmid pB-Mrk-rbsGFP, providing a higher level of GFP translation.

MG-1655 DE3 cells were transformed with one of the pAC-Ymp-B or the pAC-YC-YmP-S plasmid and one of the pB-Mrk-GFP or the pBad-Mrk-rbs-GFP plasmid (plasmid maps shown in FIGS. 5B-5E, 5H and 5I) and then analyzed over a 4 hour time course following a 1.5 hour pulse of YhjH-mChy-PopZ expression induced with 0.02 mM IPTG. The same methods described above for fluorescence microscopy and flow cytometry were used for analysis. Similar to the GFP fluorescence levels observed with the split-GFP c-di-GMP reporter system in FIG. 2E, cells containing the YhJh-mChy-PopZ biochemical platform did not exhibit GFP expression while cells lacking the YhJh-mChy-PopZ biochemical platform exhibited high GFP expression.

FIGS. 3B-3E depict GFP expression in cells transformed with pAC-YmP-S and pB-Mrk-rbsGFP plasmids. The plasmid pBad-Mrk-rbs-GFP includes a highly active ribosome binding site (RBS) for mrkAp, RBS 1200, as compared to the natural RBS 300. The stronger RBS inserted upstream of GFP by isothermal assembly. It is contemplated that by expression of the activator can be increased by replacing the weak RBS 300 with the strong RBS 1200.

Figure 3A:
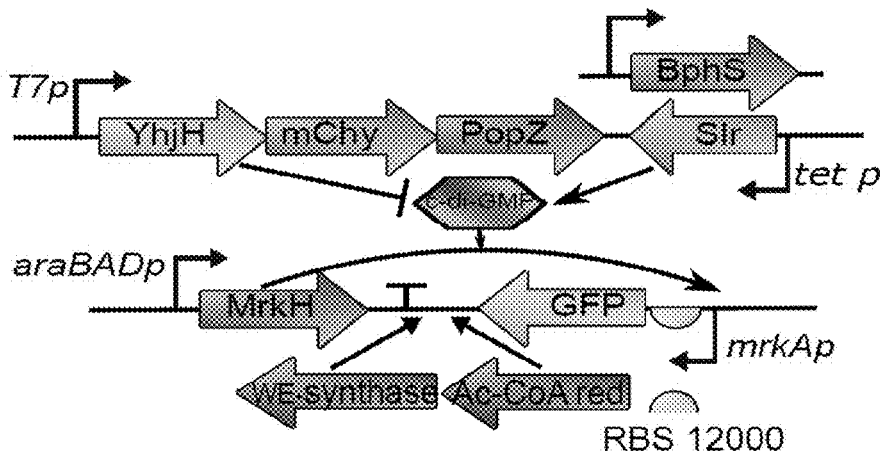
FIG. 3A illustrates a schematic diagram of a genetic circuit according to an embodiment described herein.
Figure 3B:
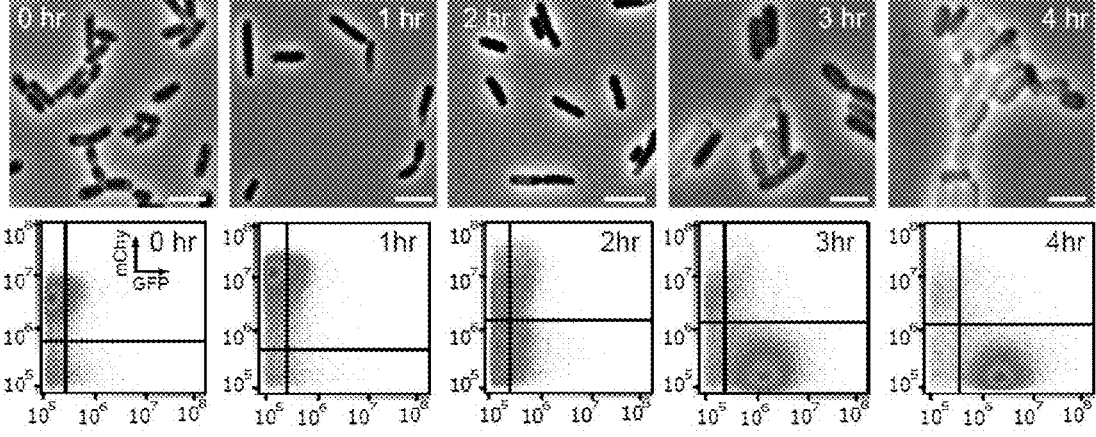
FIG. 3B illustrates images of cells at indicated times during cellular division and corresponding flow cytometry analysis of the cell populations according to an embodiment described herein.
Figure 3C:
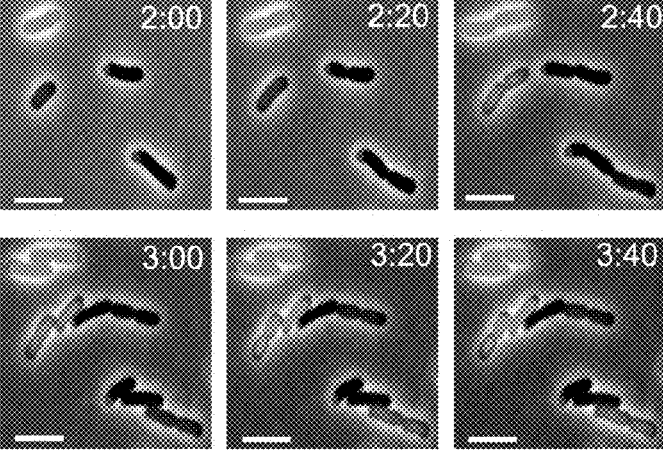
FIG. 3C illustrates images of cells at indicated times during cellular division.
Figure 3D:
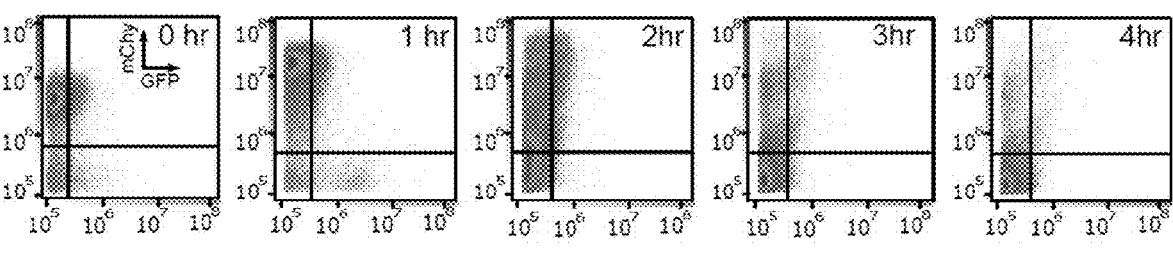
FIG. 3D illustrates flow cytometry analysis of the cell populations of FIG. 3B under modified induction conditions.
Figure 3E:
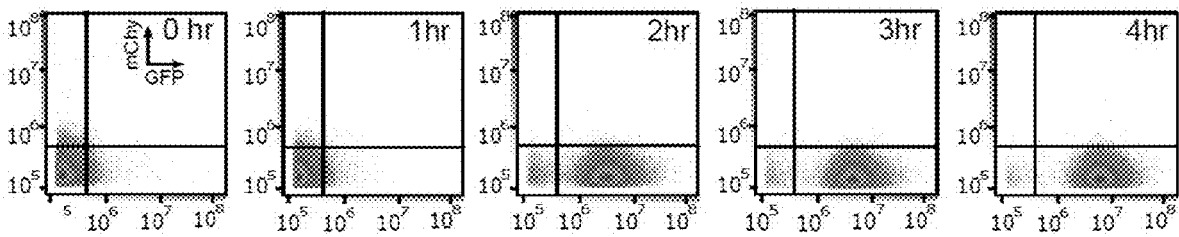
FIG. 3E illustrates flow cytometry analysis of the cell populations of FIG. 3B under modified induction conditions.

FIG. 3B includes fluorescence microphotographs of cells sequentially expressing all components of the genetic circuit in FIG. 3A (top panels) and quantitative flow cytometry analysis of the same samples (lower panels). FIG. 3C illustrates a time-lapse of the cells from FIG. 3B between the 2 hour and 4 hour mark following the 1.5 hour pulse of YhjH-mChy-PopZ expression induced with 0.02 mM IPTG. The same cells were also analyzed in conditions where either YhjH-mChy-PopZ or MrkH were not induced over the same time course, shown in FIGS. 3D and 3E. In FIG. 3D, MrkH was not expressed. In FIG. 3E, YhjH-mChy-PopZ was not expressed. Fluorescence microscopy and flow cytometry were performed using the methods described above.

Figure 3F:
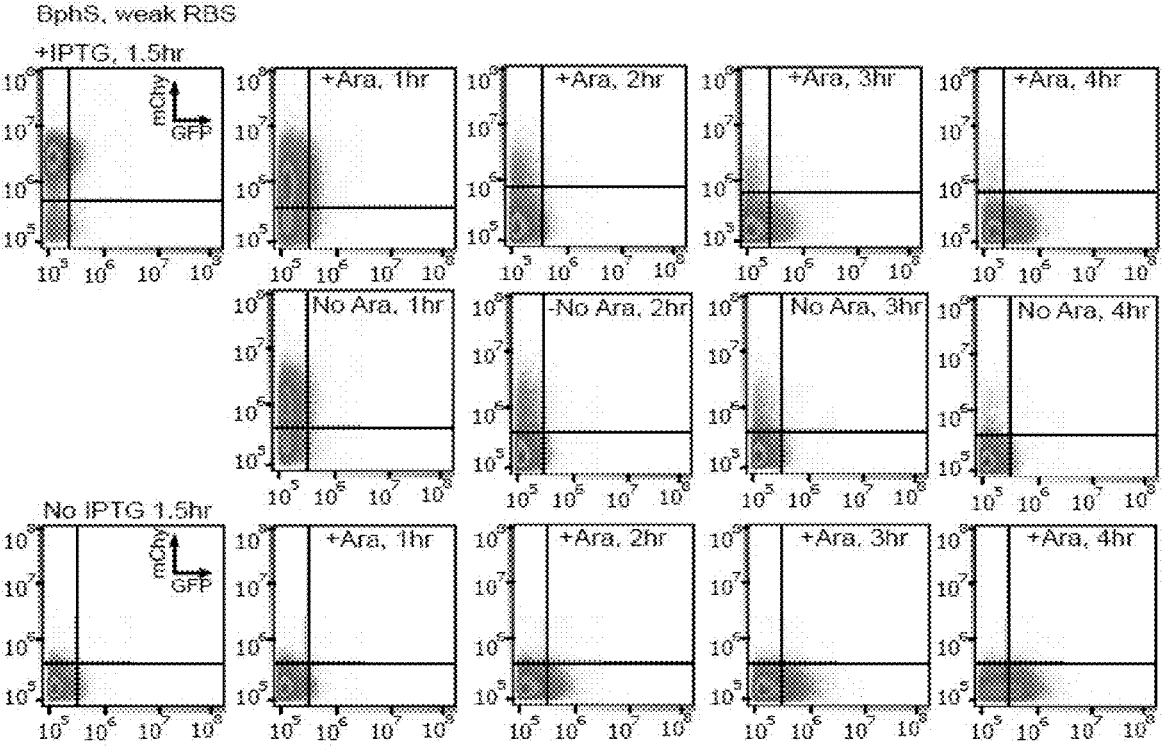
FIG. 3F illustrates flow cytometry analysis of cell populations during cellular division according to an embodiment described herein.
Figure 3G:
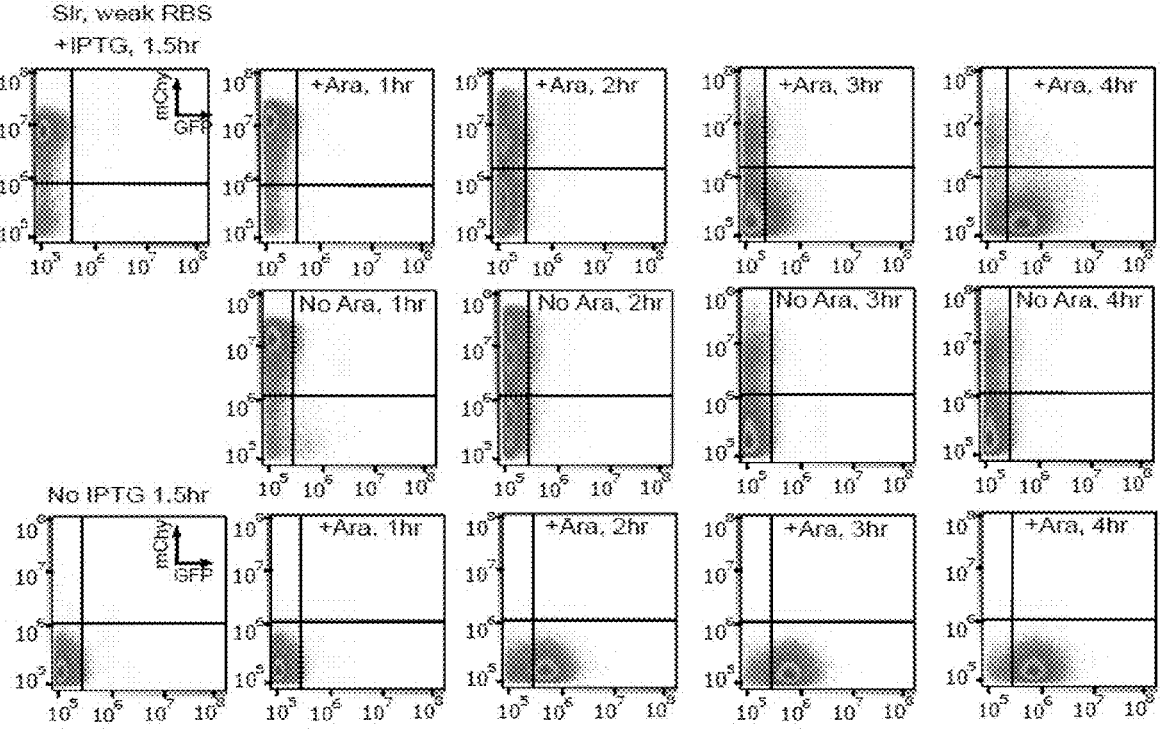
FIG. 3G illustrates flow cytometry analysis of cell populations during cellular division according to an embodiment described herein.
Figure 3H:
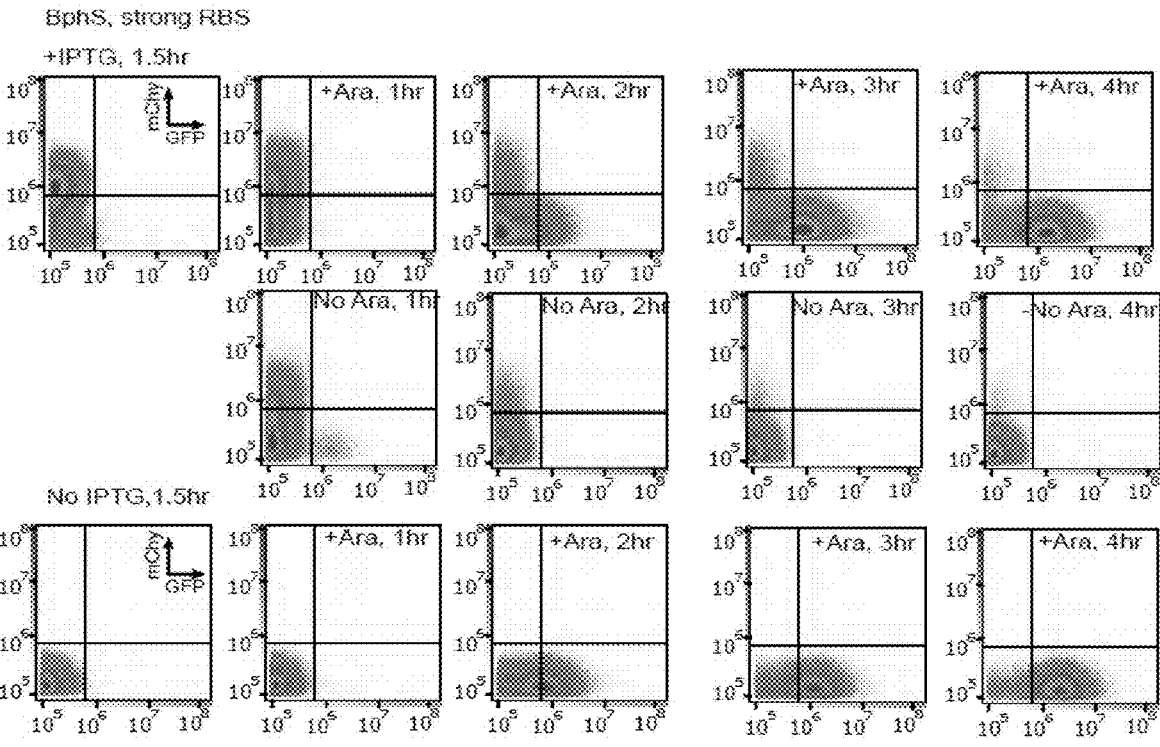
FIG. 3H illustrates flow cytometry analysis of cell populations during cellular division according to an embodiment described herein.

FIGS. 3F-3H demonstrate quantitative flow cytometry analysis of cells transformed with pAC-YmP-B or pAC-YmP-S and pB-Mrk-GFP or pB-Mrk-rbsGFP plasmids, induced to express components of the genetic circuit in the same ways as described above. As observed in the strains bearing the split-GFP reporter, the ci-di-GMP signal was higher in the presence of the more active DGC Slr1143 (FIG. 3G), as compared to BphS (FIG. 3F). GFP signals in cells bearing the plasmid pB-Mrk-rbsGFP (FIG. 3F) were consistently higher than in cells bearing the pB-Mrk-GFP plasmid (FIG. 3H), corresponding with a higher GFP translation rate.

Figures 3I, 3J:
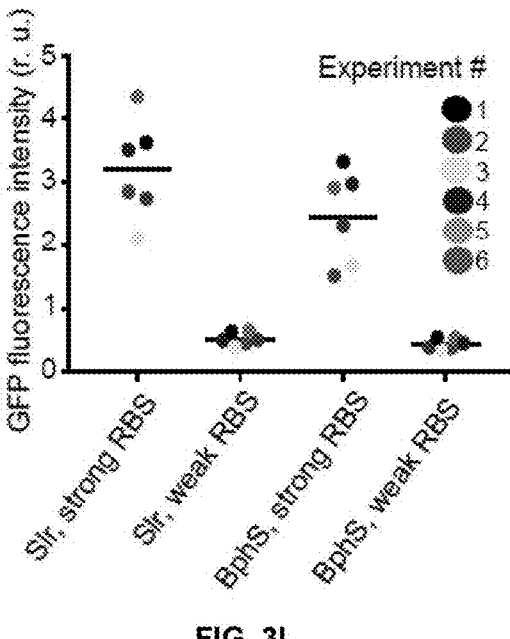
FIG. 3I is a graph illustrating GFP intensities of PopZ-negative cells from FIGS. 3A-3H at the 4 hour time point according to an embodiment described herein.
FIG. 3J is a graph illustrating the average intensity of mChy fluorescence and average number of mChy-positive cells at indicated times during cellular division according to an embodiment described herein.

FIG. 3I illustrates a data plot of the average GFP intensity of YhJh-mChy-PopZ negative cells at the 4 hour post YhjH-mChy-PopZ induction course time point in strains containing the different circuit components described in relation to FIGS. 3A-3H. Compared to the circuits using the weaker RBS300 to drive mrkH expression, the enhanced circuit with RBS1200 (SEQ ID No. 19) increased GFP signal in cells lacking YhjH-mChy-PopZ by about six-fold.

Figures 3K, 3L:
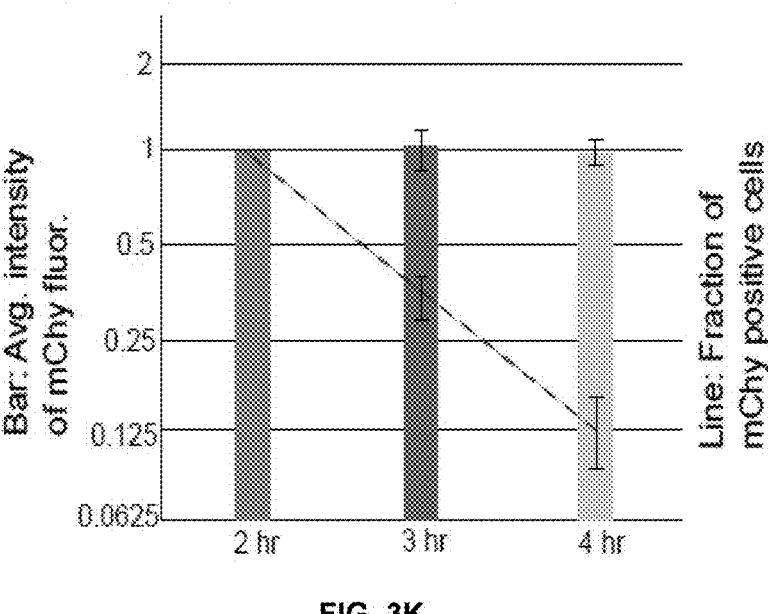
FIG. 3K is a graph illustrating the average number of YhjH-mChy-PopZ foci per cell at indicated times during cellular division according to an embodiment described herein.
FIG. 3L illustrates images of cells expressing YhjH-mChy-PopZ, followed by induction of asymmetric cell division associated with the expression of waxy ester biosynthesis in one of the cell types according to an embodiment described herein.

FIGS. 3J and 3K illustrate characterization data of the YhjH-mChy-PopZ biochemical platform. In FIG. 3J, cells were transformed with the plasmid pAC-YmP-S and analyzed by fluorescence microscopy following a 90 minute pulse of YhjH-mChy-PopZ expression. The number of YhjH-mChy-PopZ foci per cell were counted at the end of the induction period and at the end of every hour during a 4 hour time course. Following induction, an average of 59% of the cells had two or more foci, often localized near opposite cell poles. As the cells divided over time, the fraction of YhjH-mChy-PopZ positive cells with only one polar focus increased from about 40% to greater than 90%. In FIG. 3K, flow cytometry data was utilized to assess the stability of the YhjH-mChy-PopZ foci between 2 hours and 4 hours post-induction. Fluorescence intensity of mChy remained constant for multiple rounds of cell division as the fraction of mChy-positive cells declined.

The YhjH-mChy-PopZ biochemical platform was further tested to determine whether it could be used to control production of a bioproduct requiring a multi-gene biosynthetic pathway. As illustrated in the genetic circuits of FIG. 3A, the coding sequences for acyl-CoA reductase (Ac-CoA red) (SEQ ID No. 1) from the Jojoba plant and wax ester synthase (WE-synthase) (SEQ ID No. 24) from *Acinetobacter baylii* were inserted downstream of the transcriptional reporter GFP. The combined activity of these enzymes produces long-chain neutral lipids, such as those naturally found in jojoba oil and spermaceti.

Figure 5J:
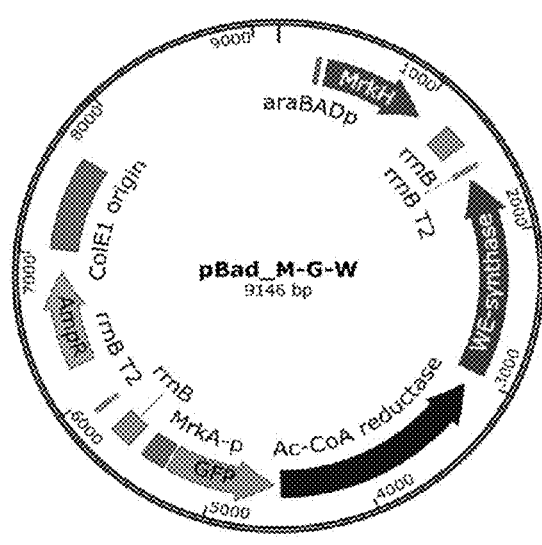
FIG. 5J illustrates a physical map of a plasmid listed in Table 1 according to an embodiment described herein.

To clone WE-synthase and Ac-CoA reductase, the WE-synthase and Ac-CoA reductase coding sequences were first cloned as a poly-cistronic message (SEQ ID No. 30) under an araBAD promoter. The gene encoding Ac-CoA reductase was codon-optimized for expression in *E. coli* and chemically synthesized. WE-synthase was PCR-amplified from *A. baylui*. Both genes were cloned into pBAD-vectors via isothermal Gibson assembly, then amplified and cloned downstream of gfp in a pCDF:pMrkA-GFP(–) plasmid (plasmid map shown in FIG. 5N). The entire sequence of mrkAp-GFP-ac-CoA reductase-WE-synthase was then amplified and cloned into a pBAD-MrkH plasmid via isothermal assembly, resulting in the plasmid pBAD-M-G-W (plasmid maps shown in FIGS. 5G and 5J, respectively).

Utilizing the multi-gene biosynthetic circuits described above and illustrated in FIG. 3A, asymmetric cell division was induced and generated daughter cells that either contained the YhjH-mChy-PopZ biochemical platform or produced neutral lipids. Thus, it is contemplated that the YhjH-mChy-PopZ biochemical platform can be utilized to generate two distinct cells within an isogenic culture having different biosynthetic pathways. In other words, cells having the YhjH-mChy-PopZ biochemical platform were non-productive, while cells lacking the biochemical platform were productive. FIG. 3L illustrates expression data of cells transformed with the pBAD-M-G-W and pAC-YmP-S plasmids, 4 hours after a pulse of YhjH-mChy-PopZ expression with MrkH induction and BODIPY staining of the lipids as variables. Samples were fixed in 4% PFA for 30 minutes, then washed in PBS and stained with the lipophilic dye BODIPY 493/50328 (488 nm) for 10 minutes. Fluorescence microscopy was performed using the methods described above, with mChy, and BODIPY (observed in Yellow (YFP) channel) signals overlaid on a phase contrast image (grayscale).

Optogenetic Control of Asymmetric Cell Division and Cell Differentiation

It is contemplated that optogenetic circuits, wherein external light exposure regulates expression of genes, may further be utilized in combination with or as an alternative to the small molecule-regulated circuits described above to control asymmetric cell division and cell differentiation. Several components of a photo-controllable transcriptional regulation system were thus incorporated into a genetic circuit to determine the feasibility of such an optogenetic circuit. These components include a light-activated histidine kinase CcaS, two additional genes hot and pcyA for synthesizing a phycocyanobilin chromophore, a cognate response regulator CcaR, and a CcaR-dependent promoter ccaRp. Upon exposure to green (535 nm) light, CcaS phosphorylates and activates CcaR, which then upregulates expression of the ccaRp promoter, located upstream of the YhjH-mChy-PopZ and thus linking the photo-controllable transcription regulation system to the production of the YhjH-mChy-PopZ biochemical platform. Furthermore, exposure to red (670 nm) light inactivates activity of the CcaS kinase.

Figure 4A:
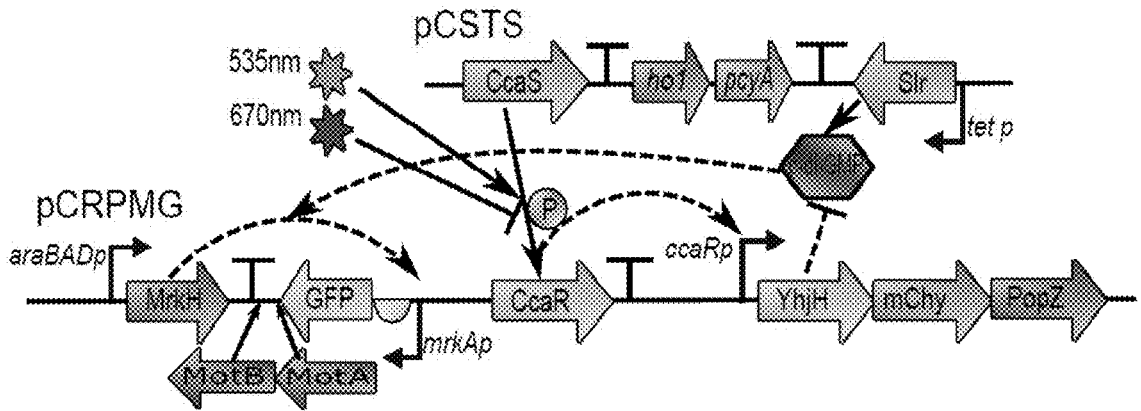
FIG. 4A illustrates a schematic diagram of a genetic circuit according to an embodiment described herein.
Figure 5P:
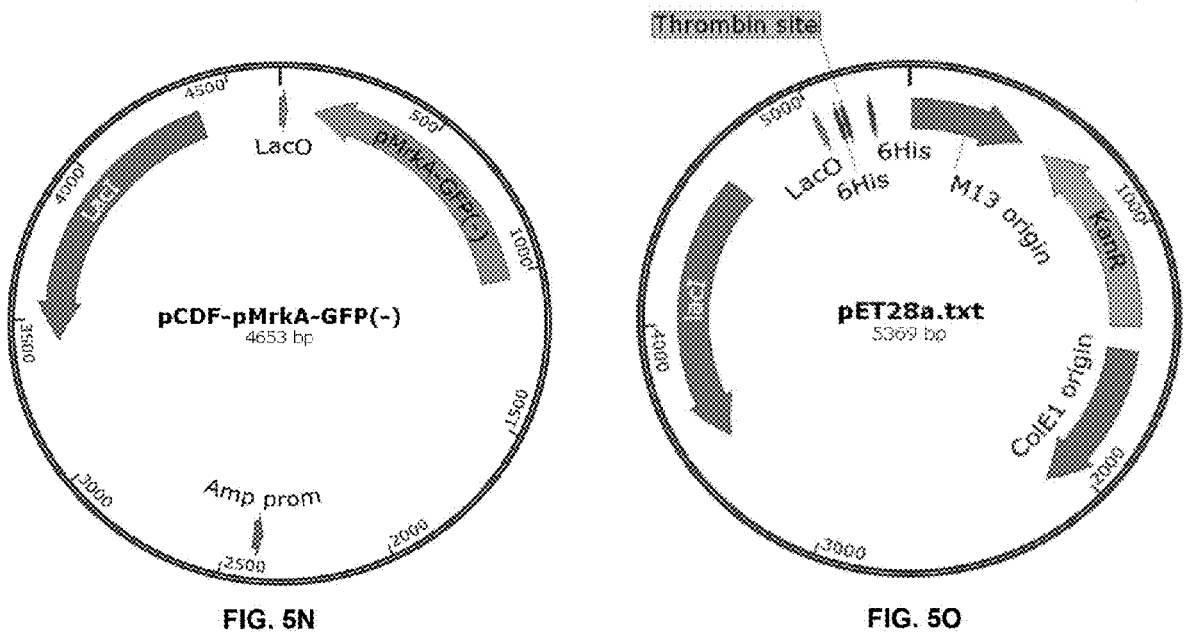
FIG. 5P illustrates a physical map of a plasmid listed in Table 1 according to an embodiment described herein.
Figure 5P:
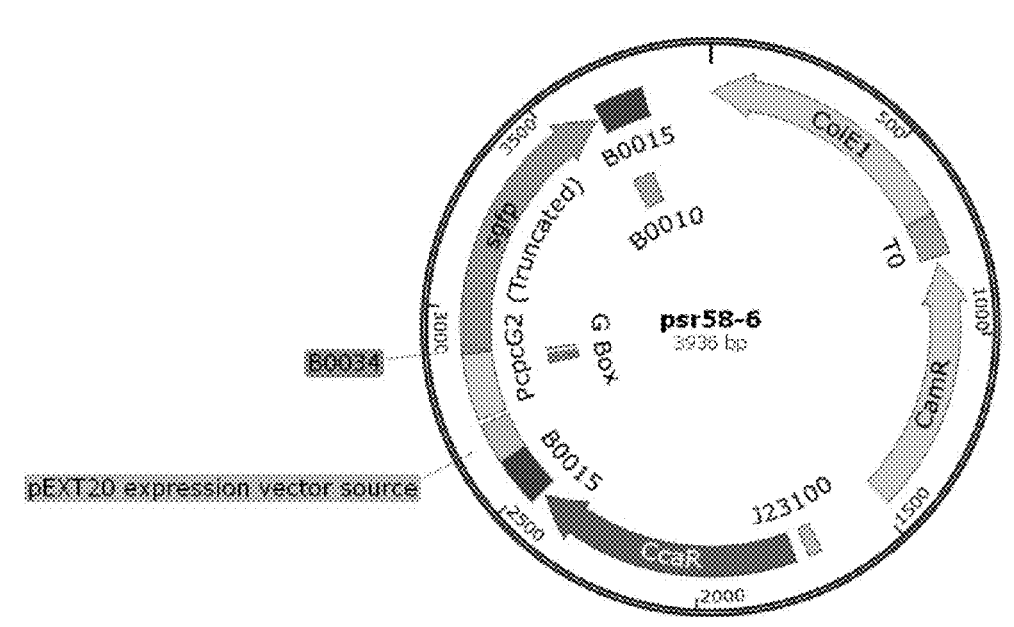
Figure 5Q:
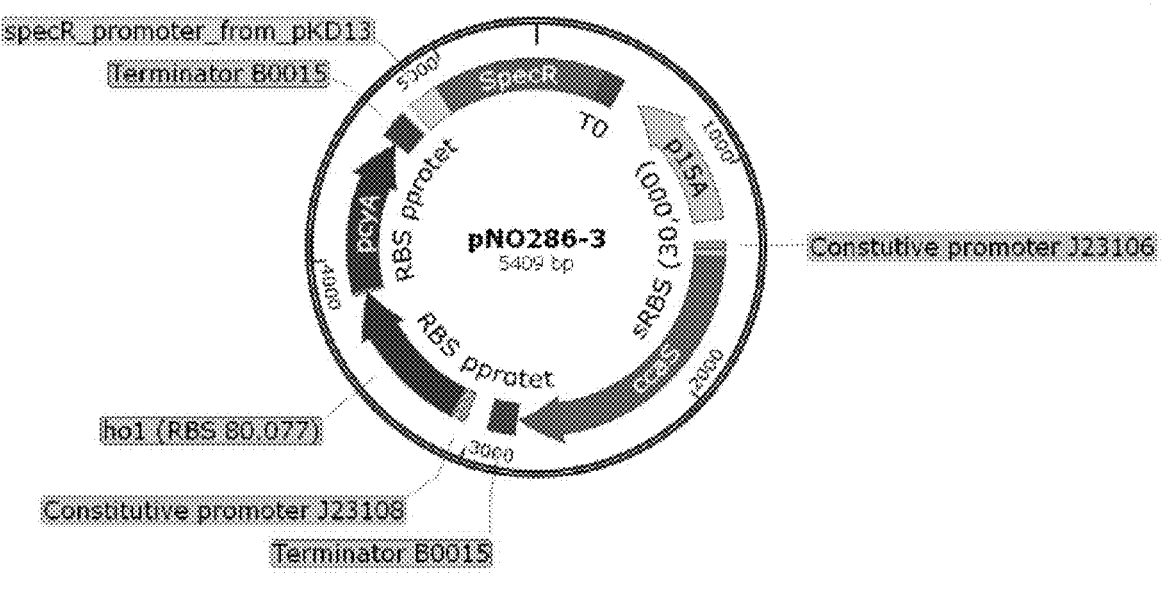
FIG. 5Q illustrates a physical map of a plasmid listed in Table 1 according to an embodiment described herein.

FIG. 4A illustrates an optogenetic circuit controllable for PopZ expression. To make the optogenetic circuit in FIG. 4A, plasmids pSR58-6 and pNO286-3 (plasmid maps shown in FIGS. 5P and 5Q, respectively) with components for light-dependent gene expression were utilized as a backbone for further cloning. The pSR58-6 plasmid was PCR linearized, excluding the gfp coding sequence, and a PCR-amplified yhjH-mChy-popZ coding sequence was inserted in place of gfp, under the PcpcG2-172 promoter (later called ccaRp), to form a pCRP plasmid (plasmid map shown in FIGS. 5K and 5M). Then, the whole message encoding araBAD-p-mrkH-mrkAp-GFP was amplified from a pb-Mrk-rbsGFP plasmid and inserted into the PCR-linearized pCRP plasmid between the CamR (SEQ ID No. 5) and CCaR genes, thus resulting in the pCRPMG plasmid (plasmid map shown in FIG. 5K; coding sequence for YhjH-mChy-PopZ platform under control of the two-component light-activated transcription activation system (CcaS/CcaR) shown in SEQ ID No. 31). The pCSTS plasmid (plasmid map shown in FIG. 5L) was formed by inserting a tet-p-slr sequence (SEQ ID Nos. 20, 23) into the pNO286-3 plasmid between the pcyA and specR genes (SEQ ID No. 21) via isothermal Gibson assembly.

To determine whether asymmetric cell division and cell differentiation could be controlled by the above optogenetic circuit, MG-1655 DE3 cells were transformed with the pCRPMG and pCSTS plasmids and grown overnight at 37° C. with illumination by 650 nm red light to inactivate CcaS kinase activity. The overnight cells were then diluted 100 times and grown in 2 ml volumes in glass tubes with vigorous shaking and illumination with alternating red and green light. The cells were exposed to 1-hour cycles of 45 minutes with 650 nm red light and 15 minutes of 535 nm green light for a total of 3 hours to induce expression of the YhjH-mChy-PopZ biochemical platform. The cells were then diluted 20 times and released in 4 ml volumes in culture tubes and incubated under red light for 2 hours with shaking. The cells were subsequently diluted 10 times to maintain growth in early log phase after first 2 hour incubation in red light.

To re-induce expression and complete the cycle of YhjH-mChy-PopZ induction, the cells were again diluted 20 times and incubated for 3 hours under alternating red and green light with shaking, as described above. The complete cycle of YhjH-mChy-PopZ induction and chase was repeated 3 times with periodic dilution, as described above, to maintain log phase growth. Appropriate antibiotics were utilized in the growth media for all stages. To express MrkH and GFP, 0.2% L-arabinose was added during the chase periods.

Figure 4B:
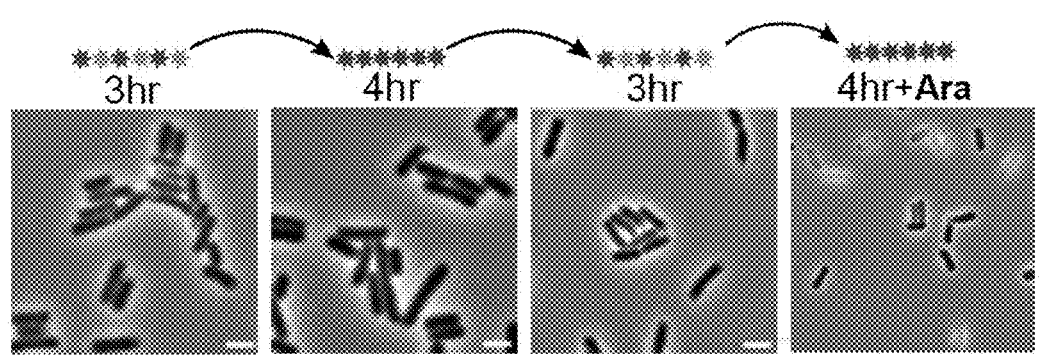
FIG. 4B illustrates images of cells at indicated times during cellular division with changing light conditions according to an embodiment described herein.
Figure 4C:
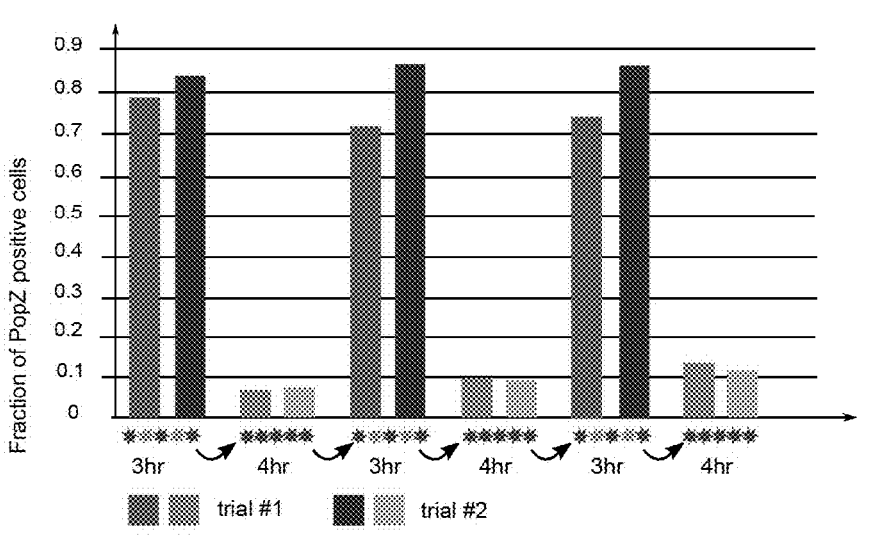
FIG. 4C is a graph illustrating the fraction of PopZ-positive cells at the indicated time points from FIG. 4B according to an embodiment described herein.

FIGS. 4B and 4C illustrate changes in the fraction of YhjH-mChy-PopZ positive cells over multiple cycles of light stimulation. FIG. 4C further depicts data from two trials of the experiment. After the four hours of incubation in red light, the fraction of YhjH-mChy-PopZ positive cells was reduced to <10%, indicating that the cells divided and produced daughter cells lacking YhjH-mChy-PopZ. During the re-induction period of alternating red and green light, it was observed that the population of YhjH-mChy-PopZ cells was restored during periods of green light exposure, and returned to about 10% during subsequent exposure to constant red light. As depicted in the last panel of FIG. 4B, when MrkH was induced by L-arabinose in this system, cells lacking YhjH-mChy-PopZ expressed the GFP reporter. Thus, it is contemplated that light can be used to modulate the ratio of cell types in the cell population for prolonged periods of time and over repeated light exposure cycles.

To demonstrate that the optogenetic circuit described above can be utilized to differentiate cells on the basis of a physical trait, coding sequences motA-motB (SEQ ID Nos. 26, 27) for MotA-MotB flagellar stator proteins, involved in powering flagellar motors were inserted in the pCRPMG plasmid downstream of gfp to form the plasmid pCRPMG-Mot (plasmid map shown in FIG. 5M) having the genetic circuit of FIG. 4A. The pCRPMG and pCSTS plasmids were then transformed into a non-motile E. coli strain MG-1655 DE3 ΔmotA-motB. To form the non-motile strain, Lambda Red recombination was used to replace part of the motA-motB coding sequence with a kanR coding sequence of the pET28a plasmid (plasmid map shown in FIG. 5O).

Figure 4D:
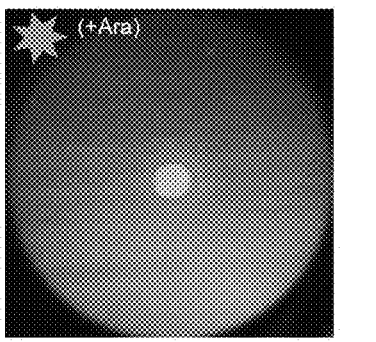
FIG. 4D illustrates images of cell motility in agar under different light regimes according to an embodiment described herein.
Figure 4D:
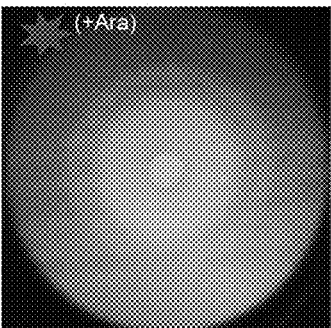
Figure 4E:
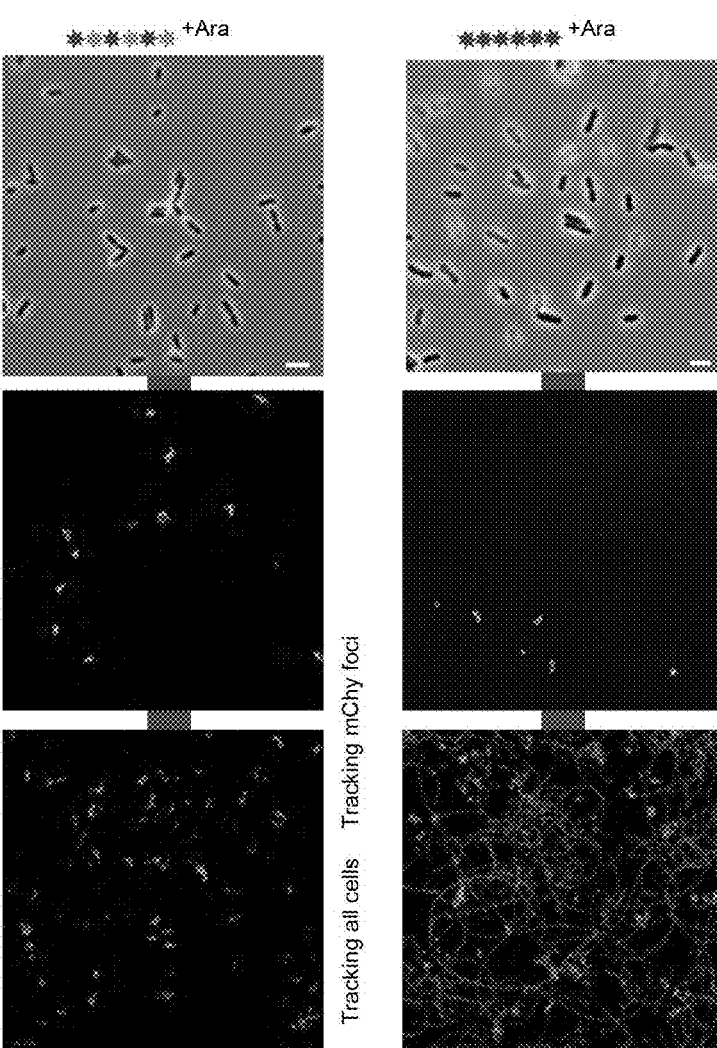
FIG. 4E illustrates images of cell motility in liquid suspension under different light regimes according to an embodiment described herein.

FIG. 4D illustrates the effects of green light exposure on cell motility of MG-1655 DE3 ΔmotA-motB cells having the motA-motB-modified optogenetic circuit described above. The MG-1655 DE3 ΔmotA-motB cells were exposed to green light (left panel) or red light (right panel) for a time course of 7 hours. Continuous exposure to red light activated mrkA expression and rescued the motility defect of the cells in soft agar. Typically, high levels of c-di-GMP normally inhibit motility. However, high levels of MotA-MotB expression induced by red light overcame this effect (over-expression of MotA was previously shown to overcome inhibiting effect of c-di-GMP on motility). As depicted in FIGS. 4E, cells were further observed by fluorescence microscopy and tracked in liquid suspension to determine whether non-motile YhjH-mChy-PopZ cells could be induced to divide asymmetrically and produce motile daughter cells. Nearly all of the cells exposed to pulsed green light contained YhjH-mChy-PopZ foci, and these cells were non-motile. By contrast, the cells that were induced to divide asymmetrically by exposure to continuous red light consisted mostly of cells that did not have YhjH-mChy-PopZ foci and instead expressed GFP and were highly motile. Thus, it is contemplated that the optogenetic circuit described above may be utilized to control gene expression and physical cell traits, such as motility, through light-regulated patterning of asymmetric cell division and cell differentiation.

In summation, embodiments of the present disclosure provide synthetic genetic circuits for facilitating asymmetric cell division and cell differentiation in microbial cultures. The novel set of genetic components described herein utilize self-assembling macromolecular complexes as geometric cues to control cell behavior and generate complex microbial communities with two or more programmable cell types. The ability to facilitate multiple cell types can further be used to express one or more desired biosynthetic pathways among the cell types, enabling division of labor and spreading the fitness costs associated with target molecule production. Still further, by enabling physiochemical control of microbial populations, the ratio of cell types within a population may be dynamically adjusted. Thus, the overall productivity of microbial cultures used in bioproduct synthesis may be increased by controlling multiple facets of the biosynthetic pathways.

While the foregoing is directed to embodiments of the present disclosure, other and further embodiments of the disclosure may be devised without departing from the basic scope thereof, and the scope thereof is determined by the claims that follow.

What is claimed is:

1. A method of establishing bacterial cell types, comprising:

introducing a nucleic acid sequence into a bacterial cell population, translationally fusing at least a first signaling protein and a second signaling protein to a PopZ protein, the PopZ protein adapted to asymmetrically localize at a first end of cells within the bacterial cell population, to form a PopZ-signaling factor complex configured to influence cell physiology;

inducing expression of the nucleic acid sequence by observing the first signaling protein;

forming first cells that contain the PopZ-signaling factor complex and second cells that do not contain the PopZ-signaling factor complex via asymmetric cell division of the cells between the first end of the cells and a second end of the cells;

introducing a small molecule in the bacterial cell population to enhance the establishment of the first cells and the second cells by observing the second signaling protein; and eliciting a different behavior in the first cells containing the PopZ-signaling factor complex and the second cells without the PopZ-signaling factor complex of the bacterial cell population.

2. The method of claim 1, wherein the PopZ protein is adapted to asymmetrically localize at a cell pole at the first end of the cells of the bacterial cell population.

3. The method of claim 1, wherein the first signaling protein is a phosphodiesterase.

4. The method of claim 3, wherein the phosphodiesterase is a c-di-GMP phosphodiesterase YhjH from E. coli.

5. The method of claim 4, wherein translationally fusing further comprises translationally fusing the c-di-GMP phosphodiesterase YhjH and a mCherry protein with a N-terminus of the PopZ protein using 9- and 12-amino acid linker sequences to form a tripartite YhjH-mChy-PopZ biochemical control platform.

6. The method of claim 5, wherein eliciting a different behavior in the first cells containing the PopZ-signaling factor complex and the second cells without the PopZ-signaling factor complex of the bacterial cell population further comprises eliciting production of wax ester synthase in the first cells containing the tripartite YhjH-mChy-PopZ biochemical control platform and no production of wax ester synthase in the second cells that do not contain the tripartite YhjH-mChy-PopZ biochemical control platform.

* * * * *